US006444205B2

(12) United States Patent
Dinsmore et al.

(10) Patent No.: US 6,444,205 B2
(45) Date of Patent: *Sep. 3, 2002

(54) TRANSPLANTATION OF NEURAL CELLS FOR THE TREATMENT OF CHRONIC PAIN OR SPASTICITY

(75) Inventors: Jonathan Dinsmore, Brookline; Julie Siegan, Boston, both of MA (US)

(73) Assignee: Diacrin, Inc., Charlestown, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/163,684

(22) Filed: Sep. 30, 1998

(51) Int. Cl.[7] ................................................ C12N 5/00
(52) U.S. Cl. ..................................................... 424/93.7
(58) Field of Search ........................... 424/93.7; 435/1.1

(56) References Cited

U.S. PATENT DOCUMENTS

| | | | | |
|---|---|---|---|---|
| 5,082,670 | A | | 1/1992 | Gage et al. .................. 424/520 |
| 5,202,120 | A | * | 4/1993 | Silver et al. ................... 424/93 |
| 5,283,058 | A | | 2/1994 | Faustman ..................... 424/88 |
| 5,330,993 | A | | 7/1994 | Armistead ................... 514/330 |
| 5,411,883 | A | | 5/1995 | Boss et al. ............... 435/240.2 |
| 5,629,194 | A | * | 5/1997 | Dinsomore ................. 435/326 |
| 5,679,340 | A | * | 10/1997 | Chappel ..................... 424/93.1 |
| 5,851,832 | A | * | 12/1998 | Weiss et al. ................ 435/368 |
| 6,140,116 | A | | 10/2000 | Dinsmore ................... 435/325 |
| 6,204,053 | B1 | | 3/2001 | Dinsmore ................... 435/325 |
| 6,258,353 | B1 | | 7/2001 | Isacson et al. ............. 424/93.1 |
| 6,277,372 | B1 | | 8/2001 | Fraser et al. ................ 424/93.7 |

FOREIGN PATENT DOCUMENTS

| | | | | |
|---|---|---|---|---|
| CA | 2204429 | * | 5/1996 | ............ C12N/5/06 |
| WO | WO 91/09936 | | 7/1991 | |
| WO | WO 92/04033 | | 3/1992 | |
| WO | WO 93/10234 | | 5/1993 | |
| WO | WO 95/12665 | | 5/1995 | |
| WO | WO 95/12982 | | 5/1995 | |
| WO | WO 95/26740 | | 10/1995 | |
| WO | WO 95/27042 | | 10/1995 | |
| WO | WO 9614398 | | 5/1996 | |
| WO | WO 9614399 | | 5/1996 | |
| WO | WO 97/02049 | | 1/1997 | |

OTHER PUBLICATIONS

Blagodatski, S. et al., "The Transplantation of Embryonic Nerve Tissue in Syringomyelia: Initial Clinical Experience," ZH Vopr Neirokhir Im N N Burdenko Vol. 3: pp. 27–29, Sep. 1994.*

Dinsmore, J. et al., "Survival of Transplanted Porcine Neural Cells Treated with F(AB')2 Antibody Fragments Directed Against Donor MHC Class–I in a Rodent Model," Transplantation Proceedings, vol. 28, No. 2: pp. 817–818, Apr. 1996.*

Falci, S. et al., "Obliteration of a Posttraumatic Spinal Cotrd Cyst with Solid Human Embryonic Spinal Cord Grafts: First Clinical Attempt," Journal of Neurotrauma vol. 14, No. 11: pp. 875–884, Nov. 1997.*

Faustman, D. et al., "Prevention of Xenograft Rejection by Masking Donor HLA Class I Antigens," Science vol. 252: pp. 1700–1702, Jun. 1991.*

Whisnant, J., ed., Clinical Medicine: Neurology, vol. 11: pp. 8–13 & 16–18, 1981.*

Wictorin, K. et al., "Axonal Outgrowth from Grafts of Human Embryonic Spinal Cord in the Lesioned Adult Rat Spinal Cord," NeuroReport 3: pp. 1045–1048, 1992.*

U.S. Congress, Off. of Technology Assessment, Neural Grafting: Repairing the Brain and Spinal Cord; pp. 105–106, Sep. 1990.*

Aihara, Noritaka et al. (1994) "Striatal Grafts In Infarct Striatopallidum Increase GABA Release, Reorganize $GABA_A$ Receptor And Improve Water–Maze Learning In The Rat" Brain Research Bulletin, vol. 33, No. 5, p. 483–488.

Akiyoshi, Donna E. (1988) "Identification of a Full–Length cDNA for an Endogenous Retrovirus of Miniature Swine" Journal of Virology, vol. 72, No. 5, p. 4503–4507.

Backlund, Erik–Olof and Miles, John (1989) "Transplantation to The Brain: A 10 years' Perspective/The Neurosurgeon In The Pain Clinic" British Journal of Neurosurgery, vol. 3, p 627–631.

Bakay, R.A.E. et al. (1985) "Preliminary Report On The Use of Fetal Tissue Transplantation to Correct MPTP–Induced Parkinson–Like Syndrome In Primates" Appl. Neurophysiol. 48:358–361.

Barinaga, Marcia (1994) "Neurotrophic Factors Enter The Clinic", Science, vol. 246, p. 772–774.

(List continued on next page.)

Primary Examiner—Jean C. Witz
(74) Attorney, Agent, or Firm—Lahive & Cockfield, LLP; Giulio A. DeConti, Jr.; Megan E. Williams

(57) ABSTRACT

Methods for using neural cells to treat chronic pain and/or spasticity are described. The neural cells can be derived from any mammal, and are preferably human or porcine in origin. The neural cells preferably are serotonergic cells or are gamma-aminobutryic acid (GABA)—producing cells. Neural cells can be obtained from adult, juvenile, embryonic or fetal donors. Neural cells can be modified to be suitable for transplantation into a subject. For example, the neural cells can be modified such that an antigen (e.g., an MHC class I antigen) on the cell surface which is capable of stimulating an immune response against the cell in a subject is altered (e.g., by contact with an anti-MHC class I antibody, or a fragment or derivative thereof) to inhibit rejection of the cell when introduced into the subject or can be genetically modified to produce a factor. In one embodiment, the neural cells are obtained from a pig which is essentially free from organisms or substances which are capable of transmitting infection or disease to the recipient subject. The neural cells of the present invention can be used to treat chronic pain and/or spasticity by delivering the cells into the spinal cord of a subject.

25 Claims, 5 Drawing Sheets

OTHER PUBLICATIONS

Beck, K.D. et al. (1995) "Mesencephalic Dopaminergic Neurons Protected by GDNF from Axotomy–Induced Degeneration In the Adult Brain" Nature 373:339–341.

Bjorklund, A. et al. (1982) "Cross–Species Neutral Grafting In A Rat Model Of Parkinson's Disease" Nature 298: 652–654.

Bjorklund, A. et al. (1984) "Intracerebral Grafting of Neuronal Cell Suspensions I. Introduction and General Methods of Preparation" Acta Physiol. Scand. Suppl. 522:1–7.

Bjorklund, A. et al. (1984) "Intracerebral Grafting of Neuronal Cell Suspensions II. Survival and Growth of Nigral Cell Suspensions Implanted In Different Brain Sites" Acta Physiol. Scand. Suppl. 522:9–18.

Bjorklund, A. et al. (1984) "Intracerebral Grafting of Neuronal Cell Suspensions VI. Survival and Growth of Intrahippocampal Implants of Septal Cells Suspensions" Acta Physiol. Scand. Suppl. 522:49–58.

Bjorklund, A et al. ((1984) "Intracerebral Grfting of Neuronal Cells Suspensions VII. Recovery of Choline Acetyltransferase Activity And Acetylcholine Synthesis In The Denervated Hippocampus Reinnvervated By Septal Suspension Implantsa" Acta Physiol. Scand. Suppl. 522:59–66.

Bonfoco, E. et al. (1995) "Apoptosis And Necrosis: Two Distinct Events Induced, Respectively, By Mild and Intense Insults With N–Methyl–D–Aspartate Or nitric Oxide/Superoxide In Cortical Cell Cultures" Proc. Natl. Acad. Sci. USA 92:7162–7166.

Borlongan, Cesario V. et al. (1996) "Will Fetal Striatal Transplants Correct The Akinetic End–Stage of Huntington's Disease?" Neurodegeneration vol. 5, No. 2, p. 189–192.

Borlongan, Cesario V. et al. (1995) "Striatal Dopamine–mediated motor Behavior Is Altered Following Occlusion of the Middle Cerebral Artery", Pharmacology Biochemistry and Behavior, vol. 52, No. 1, p. 225–229.

Borlongan, Cesario V. et al. (1995) "Locomotor and Passive Avoidance Deficits Following Occlusion of the Middle Cerebral Artery" Physiology & Behavior. vol. 58, No. 5, p. 909–917.

Brownell, Anna–Liisa et al. (1993) "In Vivo Visualization of Striatal Transplants in a Primate Model of Huntington's Disease (HD)" Journal of Nuclear Medicine vol. 34, No. 5, p. 202–203, Abstract 960.

Brustle, Oliver et al. (1992) "Angiogenic Activity of the K–fgf /hst Oncogene In Neural Transplants" Oncogene vol. 7, No. 6, p. 1177–1183.

Campbell, Kenneth et al. (1995) "Regional Incorporation and Site–Specific Differentiation of Striatal Precursors Transplanted to The Embryonic Forebrain Ventricle" Neuron, vol. 15, p. 1259–1273.

Campbell, K. et al. (1993) "Characterization of GABA Release From Intrastriatal Striatal Transplants: Dependence On Host–Derived Afferents" Neuroscience, vol. 53, No. 2, p. 403–415.

Casper, D. et al. (1991) "EGF Enhances The Survival of Dopamine Neurons In Rat Embryonic Mesencephalon Primary Cell Culture" Journal of Neuroscience Research, vol. 30, p. 372–381.

Castro, A.J. et al. 91988) "Fetal Neocortical Transplants Grafted To The Cerebral Cortex of Newborn Rats Receive Afferents from the Basal Forebrain, Locus Coeruleus and Midline Raphe" Exp Brain Res 69: 613–622.

Cattaneo, E. et al. (1993) "Transplanting Embryonic Striatal Cell Lines Into The Embryonic Rat Brain" Society For Neuroscience Abstracts, vol. 19, No. 107.6.

Chirgwin, John M. (1979) "Isolation of Biologically Active Ribonucleic Acid From Sources Enriched in Ribonuclease" Biochemistry, vol. 18, No. 24, p. 5294–5298.

Colton, C. et al. (1991) "The Effect of Xanthine/Xanthine Oxidase Generated Reactive Oxygen Species On Synaptic Transmission" Free Rad. Res. Comms. vol. 14, Nos. 5–6, p. 385–393.

Colton, Carol A. et al. (1989) "The Action of Hydrogen Peroxide On Paired Publse and Long–Term Potentiation In the Hippocampus" Free Radical Biology & Medicine, vol. 7, p. 3–8.

Colton, Carol A. et al. (1995) "Protection from Oxidation Enhances The Survival of Cultured Mesencephalic Neurons" Experimental Neurology, vol. 132, p. 54–61.

Dawson, Ted M. (1995) "Nitric Oxide: Actions And Pathological Roles", The Neuroscientist, vol. 1, No. 1, p. 7–18.

Deacon, T. et al. (1993) "Axonal Growth By Fetal Porcine Striatal Grafts In Rats" Society for Neuroscience Abstracts, vol. 19, No. 284.15.

Deacon, T.W. et al. (1993) "Target–Specific Long Distance Axon Growth From Porcine Striatal and Ventral mesencephalon Xenografts In Rats" Society for Neuroscience Abstracts, No. 205.9.

Deacon, T.W. et al. (1994) "The Lateral Ganglionic Eminence Is The Origin of Cells Committed to Striatal Phenotypes: Neural Transplantation and Developmental Evidence" Brain Research vol. 668, p. 211–219.

Deacon, T.W. et al. (1994) "Cytoarchitectonic Development, Axon–Glia Relationships, and Long Distance Axon Growth of Porcine Striatal Xenografts In Rats" Experimental Neurology, vol. 130, p. 151–167.

Drake, Christopher and Little, Charles D. (1995) "Exogenous Vascular Endothelial Growth Factor Induces Malformed And Hyperfused Vessels During Embryonic Neovascularization" Proc. Natl. Acad. Sci., vol. 92, p. 7657–7661.

Du, Xinyu and Iacovitti, Lorraine (1995) "Synergy Between Growth Factors and Transmitters Required For Catecholamine Differentiation in Brain Neurons" The Journal of Neuroscience, vol. 15, No. 7, p. 5420–5427.

Dunnett, Stephen B. et al. (1981) "Behavioural Recovery Following Transplantation of Substantia Nigra in Rats Subjected to 6–OHDA Lesions of the Nigrostriatal Pathway. I. Unilateral Lesions" Brain Research, vol. 215, p. 147–161.

Dunnett, S.B. et al. (1984) "Intracerebral Grafting of Neuronal Cell Suspensions IV. Behavioural Recovery In Rats With Unilateral 6–OHDA Lesions Following Implantation of Nigral Cell Suspensions In Different Forebrain Sites" Acta Physiol. Scand. Suppl. vol. 522, p. 29–37.

Dunnett, S.B. et al. (1984) "Intracerebral Grafting of Neuronal Cell Suspensions V. Behavioural Recovery In Rats With Bilateral 6–OHDA Lesions Following Implantation of Nigral Cell Suspensions" Acta Physiol. Scand. Suppl. vol. 522, p. 39–47.

Dunnett, Stephen B. (1995) "Functional Repair Of Striatal Systems By Neural Transplants: Evidence For Circuit Reconstruction", Behavioural Brain Research, vol. 66, p. 133–142.

Ebner, F.F. (1988) "The Development of Functional Connections Between Transplanted Embryonic and Mature Cortical Neurons" Progress in Brain Research 78: 3–11.

Elsayed, M.H. et al. (1992) "Fetal Neocortical Tissue Survives Transplantation Into A Rat Model of Neonatal Hypoxic–Ischemic Brain Damage" Society for Neuroscience Abstracts, vol. 18, No. 473.6.

Engele, Jurgen and Bohn Martha Chruchill (1991) "The Neurotrophic Effects of Fibroblast Growth Factors On Dopaminergic Neurons in vitro Are Mediated by Mesencephalic Glia" The Journal of Neuroscience, vol. 11, No. 10, p. 3070–3078.

Faustman, Denise and Coe, Chuck (1991) "Prevention of Xenograft Rejection by Masking Donor HLA class I Antigens" Science vol. 252, p. 1700–1702.

Faustman, D. and Coe, C. (1992) "Xenograft Acceptance By Masking Donor Antigens" Transplantation Proceedings, vol. 24, No. 6, p. 2854–2855.

Ferrari, G. et al. (1989) "Basic Fibroblast Growth Factor promotes The Survival and Development of Mesencephalic Neurons In Culture" Developmental Biology, vol. 133, p. 140–147.

Fishell, Gord (1995) "Striatal precursors Adopt Cortical Identities In Response To Local Cues" Development, vol. 121, p. 803–812.

Fisher, Lisa J. and Gage, Fred h. (1994) "Intracerebral Transplantation: Basic and Clinical Applications to The Neostriatum" The FASEB Journal, vol. 8, p. 489–496.

Fishman, JA (1994) "Miniature Swine As Organ Donors For Man: Strategies For prevention of Xenotransplant–Associated Infections", Xenotranplantation, vol. 1, p. 47–57.

Floeter, M.K. and E.G. Jones (1985) "Transplantation of Fetal Postmitotic Neurons To Rat Cortex: Survival, Early Pathway Choices and Long–Term Projections of Outgrowing Axons" Developmental Brain Research 22: 19–38.

Freed, William J. and Cannon–Spoor, Eleanor H. (1988) "Cortical Lesions Increase Reinnervation of the Dorsal Striatum By Substantia Nigra Grafts" Brain Research, vol. 446, p. 133–143.

Freeman, T.B. et al. (1988) "Cross–Species Intracerebral Grafting of Embryonic Swine Dopaminergic Neurons" Progress in Brian Research 78: 473–477.

Frodl, E.M. et al. (1994) "Lazaroids improve the survival of cultured rat embryonic mesencephalic neurones" NeuroReport 5:2393–2396.

Gage, F.h. et al. (1984) "Intracerebral Grafting of Neuronal Cell Suspensions VIII. Survival and Growth of Implants of Nigral and Septal Cell Suspensions in Intact Brains of Aged Rats", Acta Physiol. Scand. Suppl. vol. 522, p. 67–75.

Gagnon, Celine et al. (1993) "Grafts In The Treatment of Parkinson's Disease: Animal Models", Reviews in Neurosciences, vol. 4, No. 1, p. 17–40.

Garcia, Anthony et al. (1995) "Extensive Axonal And Glial Fiber Growth From Fetal Porcine Cortical Xenografts In The Adult Rat Cortex", Cell Transplantation, vol. 4, No. 5, p. 515–527.

Giordano, M. et al. (1993) "Immortalized Striatal Cell Lines: Further Characerization And Transplantation", Society for Neuroscience Abstracts, vol. 19, No. 107.8.

Globus, Mordecai Y.–T. et al. (1988) "Effect of Ischemia On the In Vivo Release of Striatal Dopamine, Glutamate, and γ–Aminobutyric Acid Studied By Intracerebral Microdialysis" Journal of Neurochemistry vol. 51, No. 5, p. 1455–1464.

Gonzalez, M.F. et al. (1988) "Fetal Frontal Cortex Transplanted To Injured Motor/Sensory Cortex of Adult Rats: Reciprocal Connections with Host Thalamus Demonstrated With WGA–HRP" Experimental Neurology 99: 154–165.

Gonzalez–Garcia, Maribel et al. (1995) "bcl–x is Experssed In Embryonic and postnatal Neural Tissues And Functions To Prevent Neuronal Cell Death" Proc. Natl. Acad. Sci. USA, vol. 92, p. 4304–4308.

Grabowski, M. et al. (1993) "Functional Integration of Cortical Grafts Placed In Brain Infarcts of Rats" Annals of Neurology, vol. 34, No. 3, p. 362–368.

Grabowski, M. et al. (1992) "Fetal Neocortical Grafts Implanted in Adult Hypertensive Rats with Cortical Infarcts Following a Middle Cerebral Artery Occulusion: Ingrowth of Afferent Fibers From the Host Brain" Experimental Neurology 116: 105–121.

Grandin, Temple et al. (1988) "Perfusion Method For Preparing Pig Brain Cortex For Golgi–Cox Impregnation", Stain Technology, vol. 63, No. 3, p. 177–181.

Graybiel, Ann M. et al. (1989) "Intrastriatal Grafts Derived from Fetal Striatal Primordia. I. Phenotypy and Modular Organization" the Journal of Neuroscience, vol. 9, No. 9, p. 3250–3271.

Gut, Stephan H. et al. (1989) "Solubilization and Characterisation of the Cholecystokinin$_B$ Binding Site From Pig Cerebral Cortex", European Journal of Pharmacology, vol. 172, p. 339–346.

Hagg, Theo and Varon, Silvio et al. (1993) "Ciliary Neurotrophic Factor Prevents Degeneration of Adult Rat Substantia Nigra Dopaminergic Neurons in vivo" Proc. Natl. Acad. Sci. USA, vol. 90, p. 6315–6319.

Halliwell, Barry (1989) "Protection Against Tissue Damage In Vivo By Desferrioxamine: What Is Its Mechanism of Action?" Free Radical Biology & Medicine, vol. 7, p. 635–651.

Helm, G.A. et al. (1991) "Fetal Striatal Allografts In The Rhesus Monkey: An electron Microscopic Golgi Study" Society for Neuroscience Abstracts, vol. 17, Abstract No. 359.4.

Herranz, A. et al. (1992) "Fetal Cortical Grafts: Evaluation of Connectivity Between Grafts And Host Striatum" Society for Neuroscience Abstracts, vol. 18, No. 473.5.

Hertel–Wulff, B. et al. (1994) "Long Term Survival of Pancreatic Islets in Diabetic Monkeys" Cell Transplantation 3(3): 216 (Abstract No. 20).

Hirata, A.A. and P.I. Terasaki (1972) "Masking of Human Transplantation Antigens by Divers Substances" Journal of Immunology 108(6): 1542–1550.

Huffaker, T.K. et al. (1989) "Xenografting of Fetal Pig Ventral Mesencephalon Corrects Motor Asymmetry In The Rat Model of Parkinson's Disease" Experimental Brain Research, vol. 77, p. 329–336.

Hantraye, p. et al. (1991) "Fetal Striatal Cross–Species Implants Ameliorate Abnormal Movements In A Primate Model of Huntingtons' Disease" Society for Neuroscience Abstracts, vol. 17, Abstract No. 359.3.

Hantraye, P. et al. (1992) "Intrastriatal Transplantation of Cross–Species Fetal Striatal Cells Reduces Abnormal Movements In A primate Model of Huntington Disease" Proc. Natl. Acad. Sci. USA, vol. 89, p. 4187–4191.

Hyman, Carolyn et al. (1994) "Overlapping and Distinct Actions of the Neurotrophins BDNF, NT-3, and NT-4/5 on Cultured Dopaminergic and GABAergic Neurons of the Ventral Mesencephalon" The journal of Neurosicence, vol. 14, No. 1, p. 335–347.

Isacson, O. et al. (1984) "Functional Neuronal Replacement by Frafted Striatal Neurones In The Ibotenic Acid–Lesioned Rat Striatum" Nature vol. 311, p. 458–460.

Isacson, O. et al. (1985) "Neural Grafting in a Rat Model of Huntington's Disease: Progressive Neurochemical Changes After Neostriatal Ibotenate Lesions and Striatal Tissue Grafting" Neuroscience 16(4):799–817.

Isacson, O. and M.V. Sofroniew (1992) "Neuronal Loss or Replacement in the Injured Adult Cerebral Neocortex Induces Extensive Remodeling of Intrinsic and Afferent Neural Systems" Experimental Neurology 117: 151–175;+.

Isacson, O. et al. (1989) "A Primate Model of Huntington's Disease: Cross–Species Implantation of Striatal precursor Cells To The Excitotoxically Lesioned Babbon Caudate–Putamen" Expl. Brain Research, vol. 75, p. 213–220.

Jackowski, Andre (1995) "Neural Injury Repair: Hope For The Future As Barriers to Effective CNS Regeneration Become Clearer", British Journal of Neurosurgery, vol. 9, p. 303–317; Jackowski, Andre (1995) "Neural Injury Repair: Hope For The Future As Barriers to Effective CNS Regeneration Become Clearer", British Journal of Neurosurgery, vol. 9, p. 303–317.

Kikuchi, Seiji et al. (1993) "Midkine, A Novel Neurotrophic Factor, promotes Survival of Mesencephalic neurons In Culture" Neuroscience letters, vol. 160, p. 9–12.

Knusel, Beat et al. (1990) "Selective And Nonselective Stimulation of Central Cholinergic and Dopaminergic Development In Vitro By Nerve Growth Factor, Basic Fibroblast Growth Factor, Epidermal Growth Factor, insulin and the Insulin–Like Growth Factors I and II", The Journal of Neuroscience vol. 10, No. 2, p. 558–570.

Koide, Kazuo et al. (1993) "Improvement of Passive Avoidance Task After Grafting of Fetal Striatal Cell Suspensions In Ischemic Striatum In The Rat" Restorative Neurology and Neuroscience, vol. 5, p. 205–214.

Kopin, I.J. (1993) "Parkinson's Disease: Past, Present, and Future" Neuropharmacol. 9(1): 1–12.

Kopyov, O.V. (1992) "Fetal Human and Pig Mesencephalon Xenografts Have Equal Effectiveness In Behavioral Restoration of Damaged Rat Brain" Transplantation Proceedings 24(2): 547–548.

Labandeira–Garcia, J.L. et al. (1991) "Development of Intrastriatal Striatal Grafts And Their Afferent Innervation From The Host" Neuroscience, vol. 42, No. 2, p. 407–426.

Lie, W.R et al. (1988) "Preparation and Characterization of Murine Monoclonal Antibodies To Swine Lymphocyte Antigens" Immunology, vol. 64, p. 599–605.

Lindsay, Ronald M. et al. (1994) "Neurotrophic Factors: From Molecule To Man" TINS, vol. 17, No. 5, p. 182–190.

Lindvall, O. et al. (1994) "Evidence for Long–term Survival and Function of Dopaminergic Grafts In Progressive Parkinson's Disease" Annals of Neurology 35(2): 172–180.

Lindvall, Olle (1991) "Prospects of Transplantation In Human Neurodegenerative Diseases" TINS, vol. 14, No. 8, p. 376–384.

Liu, F.C. et al. (1993) "Intrastriatal Grafts Derived From Fetal Striatal Primordia–IV. Host And Donor Neurons Are Not Intermixed" Neuroscience, vol. 55, No. 2., p. 363–372.

Lyons, Ernest W. et al. (1994) "Immunosuppressant FK506 Promotes Neurite Outgrowth In Cultures of PC12 Cells and Sensory Ganglia" Proc. Natl. Acad. Sci. USA, vol. 91, p. 3191–3195.

Macklis, J.D. (1993) "Transplanted Neocortical Neurons Migrate Selectively into Regions of Neuronal Degeneration Produced by Chromophore–targeted Laser Photolysis" Journal of Neuroscience 13(9): 3848–3863.

Madrazo (1990) "Fetal Homotransplants (Ventral Mesencephalon and Adrenal Tissue) to the Striatum of Parkinsonian Subjects" Arch Neurol, vol. 47, p. 1281–1285.

Madrazo, I. et al. (1991) "Fetal Neural Grafting For The Treatment of Huntington's Disease (HD)–Report of the First Case" Society for neuroscience Abstracts 17:902, Abstract No. 359.1.

Matsas, R. and Kenny, A.J. (1989) "Immunocytochemical Localization of Endopeptidase=24.11 In Cultured Neurons From Pig Striatum", Neuroscience, vol. 31, No. 1, p. 237–246.

McDaniel William, F. (1988) "The Behavioral Influences of Brain Tissue Transplants Following Hippocampal or Cerebral Cortex Injuries" Med. Sci. Res. vol. 16(9), p. 435–440.

McAllister II, James P. et al. (1989) "Minimal Connectivity Between Six Month Neostriatal Transplants And The Host Substantia Nigra" Brain Research, vol. 476, p. 345–350.

Merry, Diane, E. et al. (1994) "bcl–2 Protein Expression Is Widespread In The Developing Nervous System and Retained in the Adult PNS" Development vol. 120, p. 301–311.

Millauer, Birgit et al. (1993) "High Affinity VEGF Binding and Developmental Expression Suggest Flk–1 As A Major Regulator of Vasculogenesis and Angiogenesis" Cell, vol. 72, p. 835–846.

Nakao, N. et al. (1994) "Lazaroids Improve The Survival of Grafted Rat Embryonic Dopamine neurons" Proc. Natl. Acad. Sci. USA, vol. 91, p. 12408–12412.

Nakao, N. et al. (1995) "Overexpressing Cu/ZN Superoxide Dismustase Ehances Survival of Transplanted Neurons in a Rat Model of Parkinson's Disease" Nature Medicine, vol. 1, No. 3, p. 226–231.

Nishino, H. et al. (1993) "Striatal Grafts In The Ischemic Striatum Improve Pallidal GABA Release and Passive Avoidance" Brain Research Bulletin, vol.. 32, p. 517–520.

Nishino, H. et al. (1994) "Pathophysiological Process After Transient Ischemia of the Middle Cerebral Artery In the Rat" Brain Research Bulletin, vol. 35, No. 1, p. 51–56.

Norman, Andrew B. et al. (1989) "Functional Effects of Fetal Striatal Transplants" Brain Research Bulletin, vol. 22, p. 163–172.

Nunn, Julia and Hodges, Helen (1994) "Cognitive Deficits Induced By Global Cerebral Ischaemia: Relationship To Brain Damage and Reversal By Transplants" Behavioural Brain Research, vol. 65, p. 1–31.

Pakzaban, P. et al. (1995) "A Novel Mode of Immunoprotection of Neural Xenotransplants: Masking of Donor Major Histocompatibility Complex Class I Enhances Transplant Survival In The Central Nervous System" Neuroscience, vol. 65, No. 4, p. 983–996.

Pakzaban, P. et al. (1993) "Increased Proportion of Acetylcholinesterase–Rich Zones and Improved Morphological Integration In Host Striatum of Fetal Grafts Derived From The Lateral But Not The Medial Ganglionic Eminence" Experimental Brain Research 97:13–22.

Peschanski, M. et al. (1995) "Rationale For Intrastriatal Grafting of Striatal Neuroblasts In Patients With Huntington's Disease" Neuroscience vol. 68, No. 2, p. 273–285.

Pittius, C.W. et al. (1987) "Ontogenetic Development of Proenkephalin A and Proenkephalin B Messenger RNA In Fetal Pigs", *Exp Brain Res*, vol. 69, p. 208–212.

Polgar, S. et al. (1993) "Fetal Striatal Transplants and Their Relationship to Transient Hypoactivity" Society for Neuroscience Abstracts, vol. 19, No. 284.18.

Poulsen, K.T. et al. (1994) "TGFβ2 and TGFβ3 Are Potent Survival Factors For Midbrain Dopaminergic Neurons" Neuron, vol. 13, p. 1245–1252.

Prehn, Jochen H.M. et al. (1994) "Regulation of Neuronal Bcl2 Protein Expression and Calcium Homeostasis By Transforming Growth Factor Type β confers Wide–Ranging Protection on Rat hippocampal Neurons" Proc. Natl. Acad. Sci. USA, vol. 91, p. 12599–12603.

Pritzel, M. et al. (1986) "Afferent and Efferent Connections of Striatal Grafts Implanted Into the Iobtenic Acid Lesioned Neostriatum in Adult Rats" Exp. Brain Res., vol. 65, p. 112–126.

Redmond, E.D. Jr. et al. (1993) "Neural Transplantation for Neurodegenerative Diseases: Past, Present, and Future" Annals of the New York Academy of Sciences 695: 258–266.

Rutherford, A. et al. (1987) "Electrophysiological Demonstration of Host Cortical Inputs to Striatal Grafts" Neuroscience Letters, vol. 83, p. 275–281.

Santacana, M. et al. (1990) "Transplant Connectivity In the Rat Cerebral Cortex. A Carbocyanine Study" Developmental Brain Research 56: 217–222.

Schallert, Timothy et al. (1990) "Multileel Transneuronal Degeneration After Brain Damage: Behavioral Events and Effects of Anticonvulsant γ–Aminobutyric Acid–Related Drugs" Supplement III Stroke, vol. 21, No. 11, p. 143–146.

Schimidt, R.H. et al. (1984) "Intracerebral Grafting of Neuronal Cell Suspensions III. Activity of Intrastriatal Nigral Suspension Implants as Assessed by Measurements of Dopamine Synthesis and Metabolism" Acta Physiol. Scand. Suppl. vol. 522, p. 19–28.

Schwarz, S.S. and Freed, W.J. (1987) "Brain Tissue Transplantation In Noenatal Rats prevents a Lesion–Induced Syndrome of Adipsia, Aphagia and Akinesia" Exp. Brain Res, vol. 65, p. 449–454.

Sharma, H.S. et al. (1995) "Neucleotide sequence and expression of the porcine vascular endothelial growth factor" Biochimica et Biophysica Acta 1260:235–238.

Shrine, Jim (1994) Regeneron Drops Phase III of CNTF, Bioworld Today, vol. 5, No. 123, p. 1–6.

Sirinathsinghji, D.J.S. et al. (1993) "The Expression of GAP–43 mRNA in Developing Embryonic Striatal Tissue Grafts" NeuroReport, vol. 4, No. 2, p. 175–178.

Sloan, D.J. et al. (1991) "The Immune Response To Intracerebral Neural Grafts", TINS, vol. 14, No. 8, p. 341–346.

Smith, Douglas, M. (1993) "Endogeneous Retroviruses In Xenografts" New England Journal of Medicine, vol. 328, No. 2, p. 142–143.

Spector, Dennis H. et al. (1983) "A Model Three–Dimensional Culture System for Mammalian Dopaminergic Precursor Cells: Application for Functional Intracerebral Transplantation" Experimental Neurology, vol. 124, p. 253–264.

Stanfield, B.B. and D.D.M. O'Leary (1985) "Fetal Occipital Cortical Neurones Transplanted To The Rostral Cortex Can Extend and Maintain A Pyramidal Tract Axon" Nature 313: 135–137.

Stromberg, I. et al. (1994) "Glial Cell Line–Derived Neurotrophic Factor Is Expressed in the Developing but not Adult Striatum and Stimulates Developing Dopamine Neurons in Vivo" Experimental Neurology, vol. 124, p. 401–412.

Talley, A.K. et al. (1995) "Tumor Necrosis Factor Alphas–induced Apoptosis In Human Neuronal Cells: Protection by the Antioxidant N–Acetylcysteine and the Genes bcl–2 and crmA" Molecular And Cellular Biology, vol. 15, No. 5, p. 2359–2366.

Tillotson, G.L. et al. (1995) "Analysis of Neocortical Grafts Placed Into Focal Ischemic Lesions In Adult Rats" Neuroscience Letters vol. 201, p. 69–72.

Tomac, A. et al. (1995) "Protection and Repair of the Nigrostriatal Dopaminigergic System by GDNF In Vivo" Nature vol. 373, p. 335–339.

Tulipan, Noel et al. (1986) "Neonatal Striatal Grafts Prevent Lethal Syndrome Produced By Bilateral Intrastriatal Injection of Kainic Acid" Brain Research vol. 377 p. 163–167.

Tulipan, Noel et al. (1988) "Striatal Grafts Provide Sustained Protection from Kainic And Quinolinic Acid–Induced Damage" Experimental neurology, vol. 102, p. 325–332.

Van Roon, W.M.C. et al. (1995) "Fetal Porcine Ventral Mesencephalon Grafts: Dissection Procedure and Cellular Characterization In Culture" Restorative Neurology and Neuroscience 7(4): 199–205.

Volpi, R. et al. (1991) "Failure of the Gamma–Aminobutyric Acid (GABA) Derivative, Baclofen, To Stimulate Growth Hormone Secretion in Parkinson's Disease" J. Neural Transm, vol. 3(4), p. 259–264.

Walker, P.D. and J.P. McAllister II (1987) "Minimal connectivity between neostriatal transplants and the host brain" Brain Research 425:34–44.

Wictorin, K. et al. (1992) "Long Distance Directed Axonal Growth From Human Dopaminergic Mesencephalilc Neuroblasts Implanted Along the Nigrostriatal Pathway in 6–Hydroxydopamine Lesioned Adult Rats" Journal of Comparative Neurology 323: 475–494.

Wictorin, K. et al. (1991) "Long Axonal Growth in Adult Rat Striato–Nigro–Striatal System From Grafts of Human Neuroblasts" Society for Neuroscience Abstracts 17:902, Abstract No. 359.2.

Wictorin K, et al. Axon outgrowth from grafts of human embryonic spinal cord in the lesioned adult rat spinal cord. Neuroreport. Dec. 1992;3(12):1045–8.

Wolff, J.A. et al. (1989) "Grafting Fibroblasts Genetically Modified To produce L–dopa In A Rat Model of Parkinson Disease" Proc. Natl. Acad. Sci. USA 86: 9011–9014.

Wood, Matthew J.A. et al. (1993) "Specific Tolerance to Neural Allografts Induced With An Antibody To the Interleukin 2 Receptor" J. Exp. Med. vol. 177, p. 597–603.

Xu, Z.C. et al. (1991) "Restoration of Thalamostriatal Projections in Rat Neostriatal Grafts: An Electron Microscopic Analysis" The Journal of Comparative Neurology, vol. 303, p. 22–34.

Yumoto, Noboru et al. (1986) Solubilization and Characterization of Prostaglandin $E_2$ Binding Protein From Porcine Cerebral Cortex, Journal of Neurochemistry, vol. 46, No. 1, p. 125–132.

Zager, Eric L. and Black, Mcl. Peter (1988) "Neural Transplantation" Surg Neurol, vol. 29, p. 350–66.

Zhong, L.T. et al. (1993) "bcl–2 Inhibits Death of Central Neural Cells Induced By Multiple Agents" Proc. Natl. Acad. Sci. USA vol. 90, p. 4533–4537.

Zhou, H. and R.D. Lund (1992) "Neonatal Host Astrocyte Migratin Into Xenogeneic Cerebral Cortical Grafts" Developmental Brain Research 65: 127–131.

Xhou, H.F. et al. (1990) "Timing and Patterns of Astrocyte Migration From Xenogeneic Transplants fo the Cortex and Corpus Callosum" Journal of Comparative Neurology 292: 320–330.

Zhou, F.C. and N. Buchwald (1989) "Connectivities of the striatal grafts in adult rat brain: a rich afference and scant striatonigral efference" Brain Research 504:15–30.

Aebischer, P. et al. (1994) "Transplantation In Human Of Encapsulated Xenogeneic Cells Without Immunosuppression", Transplantation, ,vol. 58, No. 11, pp. 1275–1277.

Anbar, Michael et al. (1997) "Role of Nitric Oxide In The Physiopathology of Pain", Journal of Pain and Symptom Management, vol. 14, No. 4, ppp. 225–254.

Basso, D. Michele et al. (1996) "Graded Histological and Locomotor Outcomes After Spinal Cord Contusion Using the NYU Weight–Drop Device Versus Transection", Experimental Neurology, vol. 139, No. 0098, 244–256.

Basso, D.M. et al. (1996)"MASCIS Evaluation of Open Field Locomotr Scores: effects of Experience and Teamwork On Reliability", Journal of Neurotrauma vol. 13, No. 7, pp. 343–359.

Cervero, Fernando et al. (1996) "From Acute To Chronic Pain: Mechanisms and Hypotheses", Proress in Brain Research, vol. 110, pp. 1–15.

Chudler, Erich H. et al. (1995) "The Role Of The Basal Ganglia In Nociception And Pain", Pain, vol. 60, pp. 3–38.

Czech, Kimberly A. et al. (1995) "Update On Cellular Transplantation Into The CNS As A Novel Therapy For Chronic Pain", Progress In Neurobiology, vol. 46, pp. 507–529.

De Felipe, Carmen et al. (1998) "Altered Nociception, Analgesia And Agreesion In Mice Lacking The Receptor For Substance P", Nature, vol. 392, pp394–397.

Dickenson, A.H. et al. (1997) "The Pharmacology Of Excitatory And Inhibitory Amino Acid–Mediated Events In The Transmission And Modulation of Pain In The Spinal Cord", Gen. Pharmac., vol. 28, No. 5, pp. 633–638.

Dickenson, H. Anthony (1996) "Balances Between Excitatory And Inhibitory Events In The Spinal Cord and Chronic Pain", Progress In Brain Research, vol. 110, pp. 225–231.

Dray, A. et al. (1996) "New Pharmacological Strategies For Pain Relief", Annu. Rev. Pharmacol. Toxicol., vol. 36, pp. 253–280.

Dray, A (1996) "Neurogenic Mechanisms And Neuropeptides In Chronic Pain", Progress In Brain Research, vol. 110, pp. 86–94.

Eaton, M.J. (1997) "Lumbar Transplants Of Immortalized Serotonergic Neurons Alleviate Chronic Neuropathic Pain" Pain, vol. 72, pp. 59–69.

Eaton, M.J. et al. (1996) "Autocrine BDNF Secretion Enhances The Survival And Serotonergic Differentiation Of Grafted Raphe Neuronal Precursor Cells And Lumbar Transplants Alleviate Chronic Neuropathic Pain", Society For Neuroscience, vol. 22, pp. 993.

Fern, Robert et al. (1996) "Autoprotective Mechanisms In The CNS Some New Lessons From White Matter", Molecular and Chemical Neuropathology, vol. 27, pp. 107–120.

Ibuki. T, et al. (1997) "Loss Of Gaba–Immunoreactivity In The Spinal Dorsal Horn of Rats With Peripheral Nerve Injury And Promotion Of Recovery By Adrenal Medullary Grafts", Neuroscience, vol. 76, No. 3, pp. 845–858.

Joseph, J.M. et al. (1994) "Transplantation Of Encapsulated Bovine Chromaffin Cells In The Sheep Subarachnoid Space: A Preclinical Study For The Treatment Of Cancer Pain" Cell Transplantation, vol. 3, No. 5, pp. 355–364.

Lanza, Robert P. et al. "Encapsulated Cell Technology" nature Biotechnology, vol. 14, pp. 1107–1111.

Li Ping et al. (1998) "Silent Glutamatergic Synapses And Nociception In Mammalian Spinal Cord", Nature, vol. 393, pp. 695–698.

Malcangio, Marzia et al. (1996) "GABA And Its Receptors In The Spinal Cord" Trends Pharmacol. Sci., vol. 17, pp. 457–462.

Markenson, Joseph, A. (1996) "Mechanisms Of Chronic Pain" The American Journal of Medicine, vol. 101, Suppl. 1A, pp:1A–6S–1A–18S.

Meller, S.T. et al. (1993) "Nitric Oxide (NO) And Nociceptive Processing In The Spinal Cord", Pain, vol. 52, pp. 127–136.

Puttfarcken, Pamela S. et al. (1997) "Evidence For Nicotinic Receptors Potentially Modulating Nociceptive Transmission At The Level Of The Primary Sensory Neuron: Studies With F11 Cells", Journal of Neurochemistry, vol. 69, No. 3, pp. 930–938.

Russell, I. Jon (1998) "Advances In Fibromyalgia: Possible Fole For Central Neurochemicals", The American Journal Of The Medical Sciences, vol. 315, No. 6, pp. 377–384.

Sagen, Jacqueline et al. (1987) "Morphological and Functional Correlates Of Chromaffin Cell Transplants In CNS Pain Modulatory Regions", pp. 306–333; Ann. NY. Acad. Sci., vol. 495, pp. 306–333.

Saitoh, Youichi et al. (1998) "Dose–Dependent Doxycycline–Mediated Adrenocorticotropic Hormone Secretion From Encapsulated Tet–On proopiomelanocortin Neuro2A Cells In The Subarachnoid Space" Human Gene Therapy, vol. 9, pp. 997–1002.

Steiner, Joseph P. et al. (1997) "Neurotrophic Immunophilin Ligands Stimlate Structural and Functional Recovery In Neurodegenerative Animal Models", Proc. Natl. Acad. Sci, USA, vol. 94, pp. 2019–2024.

Steiner, Joseph P. et al. (1997) "Neurotrophic Actions Of Nonimmunosuppressive Analogues of Immunosuppressive Drugs FK506, Rapamycin and Cyclosporin A", Nature Medicine, vol. 3, No. 4, pp. 421–428.

Taylor Charles P. et al. (1998) "A Summary Of Mechanistic Hypotheses Of Gabapentin Pharmacology" Epilepsy Research vol. 29, pp. 233–249.

Lindvall et al., "Clinical application of cell transplantation and neurotrophic factors in CNS disorders," *Current Opinion in Neurobiology*, 4:752–757 (1994).

* cited by examiner

FIG. 5

| BEHAVIORAL TEST | BASELINE | WEEK 3 | WEEK 6 | WEEK 9 | WEEK 12 |
|---|---|---|---|---|---|
| Open Field Locomotion | | | | | |
| SALINE + CYA | N | N | N | N | N |
| LGE F'ab | N | N | N | N | N |
| Saline | N | N | N | N | N |
| LGE+CYA | N | N | N | N | N |
| Grasping | | | | | |
| SALINE + CYA | N | N | N | N | N |
| LGE F'ab | N | N | N | N | N |
| Saline | N | N | N | N | N |
| LGE+CYA | N | N | N | N | N |
| Balance Beam | | | | | |
| SALINE + CYA | N | N | N | N | N |
| LGE F'ab | N | N | N | N | N |
| Saline | N | N | N | N | N |
| LGE+CYA | N | N | N | N | N |

N = Normal Behavior Observed

TRANSPLANTATION OF NEURAL CELLS FOR THE TREATMENT OF CHRONIC PAIN OR SPASTICITY

BACKGROUND OF THE INVENTION

Sensory nerve fibers originate from neurons in the posterior root ganglia and enter the spinal cord through the posterior nerve root. The anterior and posterior nerve roots unite distal to the cord to form a mixed spinal nerve which further combines in the cervical and lumbar areas to form the cervical, brachial, and lumbosacral plexuses. Each plexus gives rise to a number of individual mixed nerves, which are distributed to the periphery to supply muscle, skin, and blood vessels. Small myelinated axons carry sensations for pain and temperature, while so-called unmyelinated axons, which are invested by Schwann cell membranes without sheath formation, carry pain and deeper ill-defined sensation. (Gilroy. 1990. Basic Neurology. Second Edition. (McGraw Hill, Inc.) p. 352).

Under normal conditions, signals (induced, for example, by thermal, mechanical, and chemical stimuli) activate nerve fiber nociceptors and these signals are conducted to the spinal cord. The signals are then transmitted to the thalamus and cerebral cortex resulting in pain awareness (Dray and Urban. 1996. *Annu. Rev. Pharmacol. Toxicol.* 36:253). Ordinarily, nociceptive pain can be beneficial in that it can serve as a warning mechanism to indicate potential tissue damage. In contrast, chronic pain conditions can develop in which a stimulus and the pain response are not related; i.e., the pain does not serve a physiologically protective purpose.

It has been estimated that 10–20% of the adult population suffer from chronic pain. (Dray and Urban. 1996. *Annu. Rev. Pharmacol. Toxicol.* 36:253). Chronic pain differs from acute pain in that it can be incessant. Chronic pathologic lesions, neurodgeneration processes, or prolonged dysfunction of parts of the peripheral or central nervous system can cause chronic pain. Chronic pain, for example, can be described as pain which persists beyond the normal healing time for a disease or injury, pain related to chronic degenerative disease or a persistent neurologic condition, pain that emerges or persists (even recurring for months to years without an identifiable cause, or as pain associated with cancer (Markinson. 1996. *Am. Journal of Medicine.* 101: 1A-6S). Exemplary chronic pain conditions can be grouped into the following exemplary groups: headache or migraine, arthritis (rheumatoid or osteogenic), back pain, musculoskeletal, neurologic or orofacial, cardiac or visceral.

The standard course of treatment for chronic pain involves a step ladder approach which begins with non-opioid analgesics and progresses from moderate opiates to potent opiates. Opiates are often used in combination with other agents. In this way, a physician is able to monitor and adjust the dose of agent to limit the undesired side effects of opioids, which include, e.g., sedation, cognitive impairment, myoclonus, addiction, tolerance, and respiratory depression. However, opiods can induce nausea, constipation, confusion, respiratory depression, and dependence. In addition, opiate tolerance is a well documented side effect observed in chronic pain patients.

Nonsteroidal antiinflammatory drugs (NSAIDs) (which are both antiinflammatory and analgesic) and are also currently used to treat pain. These classes of drugs, however, are also not without side effects. NSAIDs produce gastrointestinal disturbances, ulceration, renal damage, and hypersensitivity reactions. In addition, these drugs must be taken repeatedly to treat chronic pain and can become ineffective with time, resulting in tolerance to the drug.

In addition, current treatments are simply unable to relieve pain in many clinically severe chronic pain disorders, such as, diabetic neuropathy, cervical radiculopathy, neuralgic amyotrophy, HIV neuropathy, neuralgic amyotrophy, fibromyalgia syndrome, or post herpetic neuralgia. Other chronic conditions intractable to current medical strategies are associated with both peripheral and/or central pain such as, post spinal cord injury, muscular dystrophy, trigeminal neuralgia, phantom limb pain, causalgia, and diabetic and alcoholic polyneuropathies. In addition, spasticity of spinal cord origin (e.g., resulting from multiple sclerosis or spinal cord injury) is another condition which often resists current treatments and which can result in chronic pain.

SUMMARY OF THE INVENTION

This invention provides methods for alleviating chronic pain and/or spasticity by administering a population of neural cells to thereby treat chronic pain and/or spasticity. Preferably, such treatment results in reestablishing sensory neural pathways in the subject with chronic pain. The present invention is based, at least in part, on the discovery that neural cell populations can be administered into the spinal cord (e.g., to the subarachnoid space or to the spinal dorsal horn) of a subject to treat chronic pain and/or spasticity.

In one aspect, the invention pertains to a method of treating a subject having chronic pain and/or spasticity by administering to the subject a composition comprising a population of isolated, primary neural cells, such that chronic pain and/or spasticity is treated.

In another aspect the invention pertains to a method of treating a subject having chronic pain by administering into the spinal cord of the subject a composition comprising a population of isolated, primary neural cells such that chronic pain is treated.

In another aspect, the invention pertains to a method of treating a subject having chronic pain by administering to the subject a composition comprising a population of isolated, porcine neural cells, such that chronic pain is treated.

In yet another aspect, the invention pertains to a method of treating a subject having chronic pain by administering into the spinal cord of the subject a composition comprising a population of isolated, primary neural cells, such that chronic pain is treated.

In one embodiment, the population comprises fetal porcine neural cells.

In one embodiment, the composition is delivered into the spinal dorsal horn of the subject. In another embodiment, the composition is delivered into the spinal dorsal horn of the subject. In another embodiment, the composition is delivered into the subarachnoid space of the spinal cord.

In one embodiment, the population of neural cells secretes a neurotransmitter. In a preferred embodiment, the neural cell is a gamma-aminobutryic acid (GABA)—releasing neural cell. In another embodiment, the neural cell is a serotonergic cell.

In one embodiment, the population of neural cells comprises human cells. In another embodiment, the population of neural cell comprises fetal human cell.

In one embodiment, the population of neural cells comprises neural stem cells. In a preferred embodiment, the population of neural stem cells is of human or porcine origin.

In one embodiment, the population of neural cells comprises totipotent cells. In a preferred embodiment, the population of neural cells comprises totipotent cells that have been induced to differentiate.

In one embodiment, the population of neural cells comprises neural cells which have been induced to differentiate into a GABA-releasing cell in vitro prior to delivery.

In one embodiment, the population of neural cells comprises neural progenitor cells.

In another embodiment, the population of neural cells comprises neural progenitor cells which have been induced to differentiate into a GABA-releasing cell in vitro prior to delivery.

In one embodiment, the population of neural cells comprises a neural cell which, in unmodified form, has at least one antigen on the cell surface which is capable of stimulating an immune response against the cells in the subject, wherein the antigen on the cell surface is altered such that lysis of the neural cell does not occur upon introduction of the neural cell into the subject and the stimulation of an immune response is inhibited.

In one embodiment, prior to delivery, to the subject the population of neural cells comprises a cell which has been contacted with a non-complement fixing antibody or non-complement fixing fragment of an antibody which binds to at least one antigen on the cell surface which is capable of stimulating an immune response against the cell in the subject to alter the antigen on the cell surface such that an immune response against the cell is inhibited.

In one embodiment, the population of neural cells comprises a cell which has been contacted with at least one anti-MHC class I antibody or fragment thereof, which binds to the MHC class I antigen on the cell surface. In one embodiment, the anti-MHC class I antibody is an anti-MHC class I F(ab')$_2$ fragment.

In one embodiment, the population of neural cells comprises a cell which has been contacted with a F(ab')$_2$ fragment of a W6/32 monoclonal antibody such that an immune response against the cell is inhibited.

In one embodiment, the composition further comprises at least one of the agents or factors selected from the group consisting of neurotrophic factors and anti-inflammatory agents.

In one embodiment, the neurotrophic factor is selected from the group consisting of brain derived neurotrophic factor, ciliary neurotrophic factor, neurotrophin-3, neurotrophin 4/5, nerve growth factor, acidic fibroblast growth factor, basic fibroblast growth factor, platelet-derived growth factor, thyrotropin releasing hormone, epidermal growth factor, amphiregulin, transforming growth factor, transforming growth factor β, insulin-like growth factor.

In one embodiment, the anti-inflammatory agent is a steroid. In a preferred embodiment, the steroid is methylprednisolone. In yet another embodiment, the anti-inflammatory agent is selected from the group consisting of cyclosporin A and FK506.

In one embodiment, the neural cell is obtained from a pig which predetermined to be free from at least one organism selected from the group consisting of zoonotic, cross-placental and neurotropic organisms.

In one embodiment, the porcine cell is obtained from the lateral ganglionic eminence of the striatum. In one embodiment, the cell is obtained from the lateral ganglionic eminence of an fetal pig between about days 30 and 40 of gestation.

In one embodiment, prior to delivery to the subject, the cell is contacted with a F(ab')$_2$ fragment of a W6/32 or PT85 monoclonal antibody such that an immune response against the cell is inhibited.

In preferred embodiments, the subject is a human.

BRIEF DESCRIPTION OF THE DRAWINGS

FIG. 5 is a graph depicting that the animals in the study (test and control) showed normal locomotion (assessed using the Basso, Beattie, and Beshnahan modified locomotion open field test) and normal ability to transverse a widely spaced wire mesh (4×4 cm spaces) and balance beam.

DETAILED DESCRIPTION OF THE INVENTION

Figure 1:
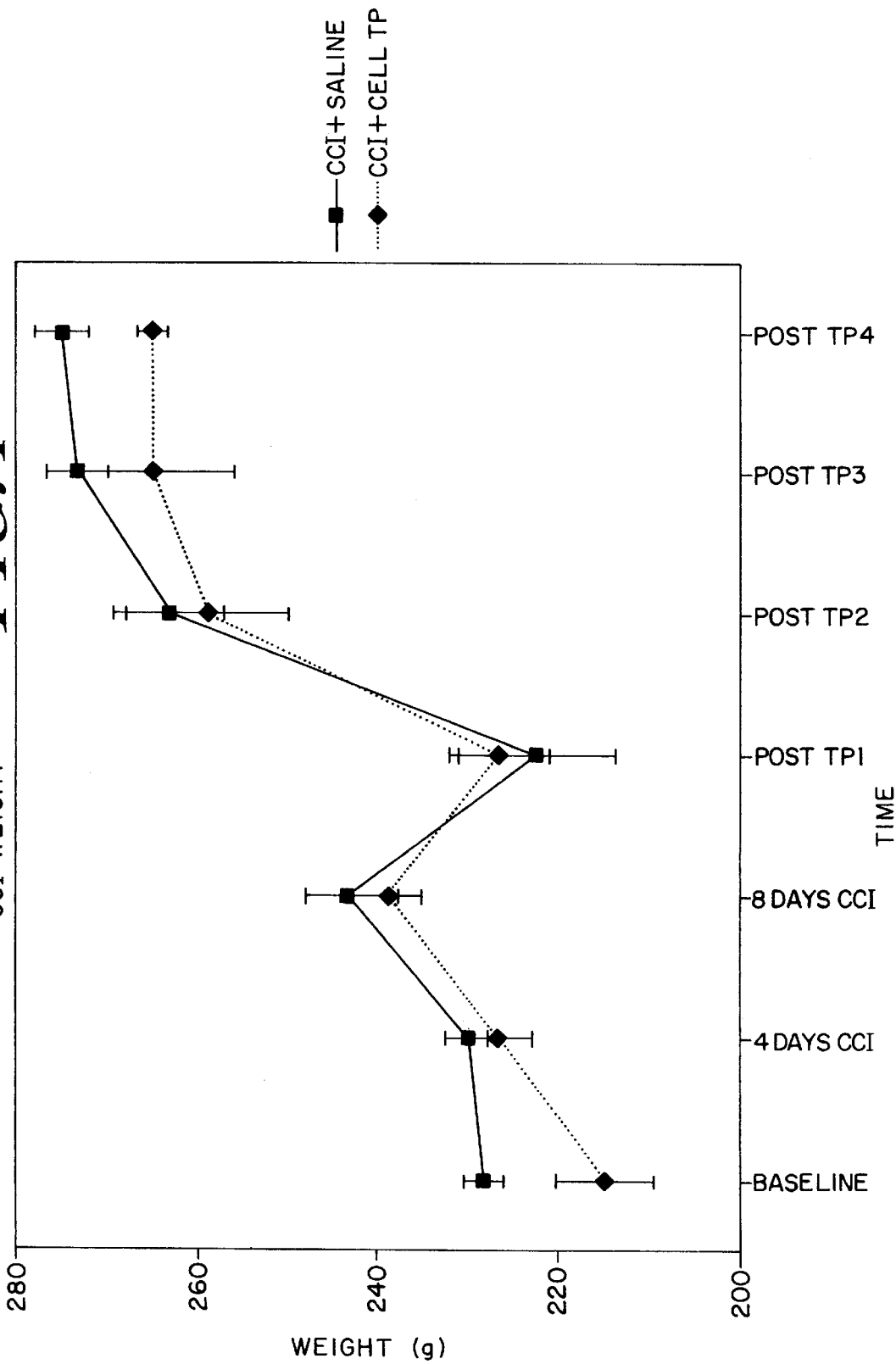
FIG. 1 is a graph depicting the weight of animals that received neural cell transplants and the animals that received control transplants was comparable.

The present invention pertains, inter alia, to the discovery that allogeneic or xenogeneic neural cells can be transplanted into subjects, preferably human subjects, to treat chronic pain and/or spasticity. The methods of the invention include administering a composition comprising a population of neural cells to a subject such that chronic pain and/or spasticity is treated.

As used herein, the following terms and phrases shall be defined as follows:

As used herein, the phrase "chronic pain" includes conditions in which pain persists and fails to respond to conventional treatment. The phrase "chronic pain" includes pain of long duration and pain that can be medically refractory. The phrase "chronic pain" also includes pain characterized by a persistent increase in the level of neuron excitability in the affected area. Exemplary chronic pain conditions include diabetic neuropathy, cervical radiculopathy, neuralgic amyotrophy, HIV neuropathy, neuralgic amyotrophy, post herpetic neuralgia, post spinal cord injury, muscular dystrophy, trigeminal neuralgia, phantom limb pain, causalgia, spasticity of spinal cord origin, and diabetic and alcoholic polyneuropathies.

As used herein, the term "spasticity" includes exaggerated tendon reflexes, clonus, and spontaneous muscle spasms, e.g., flexor or extensor spasms. In preferred embodiments, the spasticity treated by the instant methods is of spinal cord origin.

As used herein the phrase "neural cell" includes both nerve cells (i.e., neurons, e.g., uni-, bi-, or multipolar neurons) and their precursors and glial cells (e.g., macroglia such as oligodendrocytes, Schwann cells, and astrocytes, or microglia) and their precursors.

As used herein, the term "neural precursor" refers to undifferentiated neural cells such as neural stem cells and neural progenitor cells. The term "neural stem cell" as used herein refers to an undifferentiated neural cell which is capable of proliferation and results in additional neural stem cells having the ability to differentiate into neural progenitor cells under appropriate conditions. The term "neural progenitor cell" as used herein refers to undifferentiated neural cells derived from neural stem cells and which under appropriate conditions differentiate into neural cells, for example, striatal cells or mesencephalic cells. The term "neural precursor" also includes totipotent cells (e.g., cells form early stage embryos which are unrestricted in their developmental capabilities) which are induced to differentiate into neural cells. Such precursor cells can be used as sources of the neural cells, i.e., the neural cells for use in the invention can be derived from such precursor cells. As used herein, the term "derived" refers to cells which develop or differentiate from or have as ancestors totipotent stem cells and pluripotent stem cells. Methods of obtaining neural precursor cells e.g., neural stem cells and/or progenitor cells are known in the art, e.g., U.S. Pat. No. 5,753,506; WO97/44442; WO96/04368; WO94/10292; WO94/02593; Gage et al. 1995 *Ann. Rev. Neurosci.* 18:159; or WO98/30678, the contents of which are incorporated herein by reference.

The term "population" includes two or more cells. A population of cells can be obtained from the same or different source(s), e.g., the same donor or several different donors. Moreover, the cells in a population are not necessarily of the same cell type. A population of isolated neural cells can include, for example, different types of neural cells such as mature neurons and stem cells, GABA-releasing or producing neural cells, and neural cells which do not release GABA. Moreover, a population of neural cells can be associated with non-neural cells. The presence of non-neuronal cells may promote survival and growth of the neural cells upon implantation into a recipient subject. For example, glial cells or genetically modified fibroblasts can provide neurotrophic factors or substrates for spinal cord migration and remyelination.

As used herein the term "isolated" refers to a cell which has been separated from its natural environment. This term includes gross physical separation from its natural environment, e.g., removal from the donor animal. In preferred embodiments an isolated cell is not present in a tissue, i.e., the cell is separated, e.g., dissociated, from the neighboring cells with which it is normally in contact. Preferably, neural cells are administered as a cell suspension. As used herein, the phrase "cell suspension" includes cells which have been dissociated, e.g., by subjecting a piece of tissue to gentle trituration, which are in contact with a medium.

As used herein, the term "primary" includes cells which are not transformed or immortalized. The primary cells for use in the instant methods do not display the abnormal growth characteristics of tumor cells of neural origin (such as neuroblastoma cells), e.g., the cells can be contact inhibited, are not dedifferentiated, and/or do not display anchorage independent growth. Primary cells can be used after removal from a donor or can be cultured prior to transplantation into a subject.

As used herein, the term "treat" includes amelioration or reduction in pain and/or spasticity for a period of time following administration of a neural cell or population of neural cells into a subject suffering from chronic pain and/or spasticity.

The term "subject" includes mammals, e.g., primates (such as humans, and monkeys). The term "xenogeneic" as used herein refers to transplantation of cells from a donor of one species into a subject of a different species, e.g., porcine neural cells can be administered to a subject in an amount suitable to treat chronic pain and/or spasticity.

The invention is further described in the following subsections:

Cells of the Invention

Neural cells useful in the methods of this invention can be used after isolation from a donor or donors or may be obtained from in vitro culture, preferably short term in vitro culture.

Preferably, the cells of the invention are of mammalian origin, i.e., are obtained from mammalian subjects (e.g., humans, pigs, or cows). Preferred cells for use in the instant methods are porcine. Other preferred cells are human.

The cells of the invention can be selected for transplantation based upon their ability to produce a desired chemical mediator, such as a factor which controls nerve excitation, e.g., preferred cells are serotonergic (i.e., secrete 5 hydroxytryptamine (5HT)) or secrete gamma-aminobutyric acid (GABA). The presence or absence of such factors can be readily assayed using techniques which are known in the art, e.g., using a bioassay or an immunoassay. For example, a rabbit polyclonal anti-GABA antibody (Sigma, St. Louis, Mo.) can be used as described by Ibuki et al. (1997. *Neuroscience* 76:845) or an anti-5-HT antibody can be used (available from Incstar) as described by Eaton et al. (1997. *Pain* 72:59) in order to detect production of factors.

Neural cells useful in the methods of this invention may be obtained during various stages of development of the donor subject, e.g., can be embryonic fetal, juvenile, or adult cells. In general, the particular stage of development is selected based upon the intended use of the cells subsequent to storage and the species of animal from which the cells are derived.

Neural cells can be obtained from any area of the nervous system, e.g., the central nervous system including the cerebral cortex, cerebellum, midbrain, brainstem, spinal cord, ventricular tissue, or from areas of the peripheral nervous system, including the carotid body and the adrenal medulla.

In other embodiments, the cells for use in the instant methods are neural precursor cells. In one embodiment, the neural stem or progenitor cells are induced to differentiate prior to transplantation into a subject. Tissue containing stem or progenitor cells can be obtained from mammalian embryos, fetuses, juveniles, or from an adult organ donor. In preferred embodiments, stem cells to be used in the instant methods are porcine cells. In other preferred embodiments, stem cells to be used in the instant methods are human cells. In certain embodiments, autologous stem cells from the donor may be obtained, differentiated and transplanted using the instant methods.

Neural precursor cells can be obtained from any area of the central nervous system, including the cerebral cortex, cerebellum, midbrain, brainstem, spinal cord, ventricular tissue, or from areas of the peripheral nervous system, including the carotid body and the adrenal medulla. Methods of obtaining neural progenitor or stem cells are known in the art (see e.g., U.S. Pat. No. 5,753,506; WO97/44442; WO96/04368; WO94/10292; WO94/02593; Gage et al. 1995 *Ann. Rev. Neurosci.* 18:159; or WO98/30678).

To expand a population of neural cells, (e.g., stem or progenitor cells) the cells can be grown in the presence of trophic factors, such as nerve growth factor, acidic fibroblast growth factor, basic fibroblast growth factor, platelet-derived growth factor, thyrotropin releasing hormone, epidermal growth factor, amphiregulin, transforming growth factor, transforming growth factor β, insulin-like growth factor, or other growth factors using methods known in the art (see, e.g., U.S. Pat. Nos. 5,753,506, 5,612,211, 5,512, 661, WO93/01275; Mehler and Kessler. 1995 *Crit. Rev. Neurobiol.* 9:419; and WO 98/30678).

In other embodiments, neural stem cells can be induced to differentiate using agents which are known in the art, e.g., retinoic acid, butyrate, triodo-thyronine, or s-laminin.

In one embodiment, the cells for use in the present invention are fetal or embryonic cells. Preferably, the cells are derived from the fetal central nervous system. In another embodiment, the fetal cells are spinal cord cells. In preferred embodiments, the fetal cells are ventral mesencephalic cells. In still other preferred embodiments, the fetal cells are striatal cells. In yet other preferred embodiments, the striatal cells are obtained from a lateral ganglionic eminence of the striatum. In other embodiments, the fetal cells are cortical cells.

In one embodiment, the cells are fetal human cells are obtained from fetuses ranging in age from 7 to 18 weeks of gestation. In preferred embodiments, fetal human cells are obtained at between 7 and 11 weeks gestation. Fetal human cells for use in the claimed methods are obtained using methods known in the art and as required under the guidelines for use of human tissue (see e.g., DHEW publication OS 1975).

In one embodiment, neural cells for use in the invention are porcine embryonic cells which are isolated from porcine fetuses and which display the desired characteristics for transplantation. The preferred morphology of neural cells is the characteristic normal morphology of a neuron including a small rounded cell body which does not adhere to the culture vehicle, e.g., culture dish, as strongly as glial cells, which tend to have a cell body that is relatively flat. Normal neuron morphology also generally includes the presence of neurite processes. Thus, it is preferred that at least about 1%, more preferably at least about 10%, yet more preferably at least about 20%, still more preferably at least about 30%, and most preferably at least about 40% of the neural cells in culture have the characteristic neuron morphology at the time they are harvested for transplantation. As used herein the phrase "neural process" includes any extension of the cell, e.g., an axon or a dendrite in a neuron or a membranous process which forms a myelin sheath around axons in a glial cell, for example, an oligodendrocyte. See Kandel, E. R. and Schwartz, J. H. eds. (1991) Principles of Neural Science, 3rd ed. (Elsevier, New York) pp. 14–19.

In embodiments in which fetal porcine cells are used, preferably the cells are obtained between about days 20 and 115 of gestation, depending on the cell type to be isolated. For example, in certain embodiments, e.g., when the cells are porcine ventral mesencephalic cells, the cells are obtained between about days 25 and 28 of gestation. Preferably the porcine VM cells are used between about days 26 and 27 of gestation. More preferably, the porcine VM cells are used at about 27 days of gestation. In the case of fetal porcine striatal cells, preferably the cells are obtained from a fetus at between about days 30 and 50 of gestation. In more preferred embodiments, the porcine striatal cells are obtained from a fetus between about days 31 and 38 of gestation. In particularly preferred embodiments, the porcine striatal cells are obtained from a fetus between about days 34 and 36 of gestation. In the case of porcine cortical cells, the cells are preferably obtained from a fetus between about days 20 and 30 of gestation. In particularly preferred embodiments, the porcine cortical cells are obtained from a fetus between about days 24 and 28 of gestation.

In preferred embodiments, the cells for use in the instant invention are porcine striatal cells. The striatum or corpus striatum is a structure in the cerebral hemispheres consisting of two basal ganglia (the caudate nucleus and the putamen) and the fibers of the internal capsule that separate them. The porcine striatal cells of the invention are preferably obtained from a ganglionic eminence (i.e., the lateral and/or medial ganglionic eminence) of the striatum, but are more preferably obtained from a lateral ganglionic eminence of porcine striatum at the preferred gestational age described herein. The optimal age for isolation of striatal cells from embryonic pigs is between about twenty (20) and about fifty (50) days, more preferably about thirty (30) and forty (40) days, yet more preferably about thirty-one (31) and about thirty-eight (38) days, and most preferably about thirty-four (34) and about thirty-six (36) days of gestation. After about fifty (50), more preferably about forty (40), and most preferably about thirty-eight (38) or thirty-nine (39) days, the appropriate target tissue in the striatum cannot be reliably dissected and the quality of grafts post-transplantation is inferior. Thus, embryonic porcine striatal cells suitable for transplantation into humans are preferably obtained from embryonic pigs between about twenty (20) and about fifty (50) days, more preferably about thirty (30) and forty (40) days, yet more preferably about thirty-one (31) and about thirty-eight (38) days, and most preferably about thirty-four (34) and about thirty-six (36) days of gestation.

Cells Isolated from Essentially Pathogen-Free Swine

In another embodiment, the neural cells of the invention are cells determined to be free from at least one organism which originates in the animal from which the cells are obtained and which transmits infection or disease to a recipient subject. Neural cells with these characteristics can be obtained by screening the animal to determine if it is essentially free from organisms or substances which are capable of transmitting infection or disease to a xenogeneic recipient, e.g., a human recipient, of the cells. Typically, the cells are porcine cells which are obtained from a swine which predetermined to be essentially free from pathogens which detrimentally affect humans. For example, the pathogens from which the swine are free include, but are not limited to, one or more of pathogens from the following categories of pathogens: zoonotic, cross-placental and neurotropic organisms. As used herein, "zoonotic" refers to organisms which can be transferred from pigs to man under natural conditions; "cross-placental" refers to organisms capable of crossing the placenta from mother to fetus; and "neurotropic" refers to organisms which selectively infect neural cells. Within each of these categories, the organism can be a parasite, bacterium, mycoplasma, and/or virus. For example, the swine can be free from parasites (e.g., toxoplasma, *Eperythrozoon suis, Eperythrozoon parvum*), bacteria (e.g., Brucella, Listeria, *Mycobacterium TB*, Leptospirillum, H, or *Haemophilus suis*), mycoplasma (e.g., *M hyopneumonia*), and/or viruses (e.g., porcine respiratory reproductive syndrome, rabies, pseudorabies, parvovirus, encephalomyocardidis virus, swine vesicular disease, techen (porcine polio virus), hemaglutinating encephalomyocarditis, suipoxvirus, swine influenza type A, adenovirus, transmissible gastroenteritus virus, bovine viral diarrhea, vesicular stomatitis virus). Swine can also bee free from cross-placental parasites (e.g., eperythozoon suis or toxoplasma), neurotropic parasites (e.g., toxoplasma), and/or mycoplasma, such as M. hyopneumonia. Additionally, the swine can be free from bacteria such as zoonotic bacteria (e.g., brucella, listeria, *Mycobacterium TB*, leptospirillum), cross-placental bacteria (e.g., brucella, listeria, leptospirillum) and/or neurotropic bacteria (e.g., listeria). Additionally, the swine can be free from viruses such as zoonotic viruses, viruses that can cross the placenta in pregnant sows and neurotropic viruses. Zoonotic viruses include, for example, a virus in the rabies virus group, a herpes-like virus which causes pseudorabies, encephalomyocarditis virus, swine influenza Type A, transmissible gastroenteritis virus, parainfluenza virus 3 and vesicular stomatitis virus. Cross-placental viruses include, for example, viruses that cause porcine respiratory reproductive syndrome, a virus in the rabies virus group, a herpes-like virus which causes pseudorabies, parvovirus, a virus that causes swine vesicular disease, teschen (porcine polio virus), hemmaglutinating encephalomyocarditis, cytomegalovirus, suipoxvirus, and swine influenza type A. Neurotropic viruses include, for example, a virus in the rabies virus group, a herpes-like virus which causes pseudorabies, parvovirus, encephalomyocarditis virus, a virus which causes swine vesicular disease, porcine poliovirus (teschen), a virus which causes hemmaglutinating encephalomyocarditis, adenovirus, parainfluenza 3 virus.

In one embodiment, the pigs from which the spinal cord cells are isolated are essentially free from the following organisms: Toxoplasma, eperythrozoon, brucella, listeria, *Mycobacterium TB,* leptospirillum, haemophillus suis, M. Hyopneumonia, a virus which causes porcine respiratory reproductive syndrome, a virus which causes rabies, a virus which causes pseudorabies, parvovirus, encephalomyocarditis virus, a virus which causes swine vesicular disease, porcine polio virus (teschen), a virus which causes hemagglutinating encephalomyocarditis, suipoxvirus, swine influenza type A, adenovirus, transmissible gastroenteritis virus, a virus which causes bovine viral diarrhea, and vesicular stomatitis virus. The phrase "essentially free from organisms or substances which are capable of transmitting infection or disease to a xenogeneic recipient" (also referred to herein as "essentially pathogen-free") when referring to a swine from which cells are isolated or to the cells themselves means that swine does not contain organisms or substances in an amount which transmits infection or disease to a xenogeneic recipient, e.g. a human. Example III provides representative, but not limiting, examples of methods for selecting swine which are essentially free from various organisms. The cells of the invention can be isolated from embryonic or postnatal swine which are determined to be essentially free of such organisms. These swine are maintained under suitable conditions until used as a source of cells for transplantation.

Optimal gestational ages of the swine from which these cells are isolated are described in detail herein. Porcine neural cells isolated from essentially pathogen-free swine can additionally be modified to reduce the immunogenecity of the cells upon transplantation into a subject as described herein.

Modification of Neural Cells

In unmodified form, the neural cells of the invention have at least one antigen on the cell surface which is capable of stimulating an immune response against the cell in a subject. To inhibit rejection of the cell when introduced into the subject, the antigen on the cell surface is altered prior to transplantation. In an unaltered state, the antigen on the cell surface stimulates an immune response against the cell when the cell is administered to a subject (also referred to herein as recipient or recipient subject). By altering the antigen, the normal immunological recognition of the porcine neural cell by the immune system cells of the recipient is disrupted and additionally, "abnormal" immunological recognition of this altered form of the antigen can lead to cell-specific long term unresponsiveness in the recipient. It is likely that alteration of an antigen on the cell prior to introducing the cell into a subject interferes with the initial phase of recognition of the neural cell by the cells of the host's immune system subsequent to administration of the cell. Furthermore, alteration of the antigen may induce immunological nonresponsiveness or tolerance, thereby preventing the induction of the effector phases of an immune response (e.g., cytotoxic T cell generation, antibody production etc.) which are ultimately responsible for rejection of foreign cells in a normal immune response. As used herein, the term "altered" encompasses changes that are made to at least one neural cell antigen(s) which reduces the immunogenicity of the antigen to thereby interfere with immunological recognition of the antigen(s) by the recipient's immune system.

Antigens to be altered according to the current invention include antigens on a neural cell which can interact with an immune cell in a recipient subject and thereby stimulate a specific immune response against the neural cell in the recipient. The interaction between the antigen and the immune cell may be an indirect interaction (e.g., mediated by soluble factors which induce a response in the immune cell, e.g., humoral) or, preferably, is a direct interaction between the antigen and a molecule present on the surface of the immune cell (i.e., cell mediated). As used herein, the term "immune cell" is intended to include a cell which plays a role in specific immunity (e.g., is involved in an immune response) or plays a role in natural immunity. Examples of immune cells include all distinct classes of lymphocytes (T lymphocytes, such as helper T cells and cytotoxic T cells, B lymphocytes, and natural killer cells), monocytes, macrophages, other antigen presenting cells, dendritic cells, and leukocytes (e.g., neutrophils, eosinophils, and basophils). In a preferred embodiment, the antigen is one which interacts with a T lymphocyte in the recipient (e.g., the antigen normally binds to a receptor on the surface of a T lymphocyte).

In one embodiment, the antigen on the neural cell to be altered is an MHC class I antigen. Alternatively, an adhesion molecule on the cell surface, such as NCAM-1 or ICAM-1, can be altered. An antigen which stimulates a cellular immune response against the cell, such as an MHC class I antigen, can be altered prior to transplantation by contacting the cell with a molecule which binds to the antigen. A preferred molecule for binding to the antigen is an antibody, or fragment thereof (e.g., an anti-MHC class I antibody, or fragment thereof, an anti-ICAM-1 antibody or fragment thereof, an anti-LFA-3 antibody or fragment thereof, or an anti-$\beta_2$ microglobulin antibody or fragment thereof). A preferred antibody fragment is an F(ab')$_2$ fragment. Polyclonal or, more preferably, monoclonal antibodies can be used. Other molecules which can be used to alter an antigen (e.g., an MHC class I antigen) include peptides and small organic molecules which bind to the antigen. Furthermore, two or more different epitopes on the same or different antigens on the cell surface can be altered. A particularly preferred monoclonal antibody for alteration of MHC class I antigens on porcine spinal cord cells is PT85 (e.g., PT85A or PT85B; commercially available from Veterinary Medicine Research Development, Pullman Wash.). PT85 can be used alone to alter MHC class I antigens or, if each antibody is specific for a different epitope, PT85 can be used in combination with another antibody known to bind MHC class I antigens to alter the antigens on the cell surface. In addition, the monoclonal antibody W6/32 can be used. Suitable methods for altering a surface antigen on a cell for transplantation are described in greater detail in Faustman and Coe. 1991. *Science* 252:1700–1702 and PCT publication WO 92/04033. Methods for altering multiple epitopes on a surface antigen on a cell for transplantation are described in greater detail in PCT publication WO 95/26741, the contents of which are incorporated herein by reference.

Genetic Modification of Neural Cells For Treatment of Chronic Pain

In another embodiment, the neural cells of the invention are genetically engineered to express and/or secrete a foreign molecule (e.g., a heterologous molecule not normally made by the cell) or to modify the production of a molecule to treat chronic pain. Such molecules can be produced by the cells upon introduction of heterologous nucleic acid molecules using techniques which are well known in the art. Exemplary foreign molecules can, for example, directly reduce pain in the subject, can promote success of transplantation (e.g., by downmodulation of an immune response in the subject), and/or can promote survival or function of the transplanted cells. Exemplary molecules include, e.g., a neurotrophic factor, a neurotransmitter, or a neuroprotective agent. In one embodiment a foreign molecule enhances the neuroregenerative capacity of the transplanted cells, aids in reestablishing sensorineural communication of GABA interneurons, and/or aids in reestablishment of the excitatory/inhibitory neurotransmitter balance in the subject.

For example, in one embodiment, the neural cells of the invention can be modified to express nicotinic acetylcholine receptors (e.g., Puttfarcken et al. 1997. *J of Neurochemistry*. 69:930 or J. Pharmacol. Exp. Ther. 1998. 285:787). In another embodiment, the neural cells of the invention are modified to produce a factor, e.g., 5HT or GABA.

In addition, unmodified or modified neural cells can be introduced e.g., into the spinal cord of a subject, together with other types of cells (e.g., other cells of the nervous system or cells derived from other sources) which have been genetically modified to perform a useful function. For example, in order to promote growth of neurons the neural cells can be implanted into the spinal area together with other cells which secrete or have been modified to secrete, for example, a neurotrophic factor. Examples of cells that act as carriers of transgenes to a subject include fibroblasts (Fisher, L. J. et al. 1991. *Neuron* 6:371–380; Rosenberg, M. B. et al. 1988. *Science* 242:1575), adrenal chromaffin cells (Cunningham, L. A. et al. 1991. *Brain Res.* 561:192), astrocytes (Suhr, S. T. and Gage, F. H. 1993. *Arch. Neurol.* 50:1252), and myoblasts (Jiao, S. et al. 1993. *Nature* 362:450; Jiao, S. et al. 1992. *Brain Res.* 575:143; Jiao, S. et al. 1992. *Hum. Gene Ther.* 3:21). Such cells, e.g., fibroblasts and glial cells, can also be used to deliver retroviruses containing genes, e.g., herpes simplex thymidine kinase gene, the gene products of which are targets for other therapeutic drugs or agents, e.g., ganciclovir, to target cells, e.g., tumor cells, to inhibit their growth. Culver, K. et al. 1992. *Science* 256:1550; Chen, S-H. et al. 1994. *Proc. Natl. Acad. Sci.* USA 91:3054.

A cell to be introduced into the subject can be genetically modified in vitro prior to transplantation, or alternatively, the cell can be directly modified in vivo following transplantation. Suhr, S. T. and Gage, F. H. 1993. *Arch. Neurol.* 50:1252–1268; Gage, F. H. et al. (1987) *Neuroscience* 23:795–807. Various methods are available for genetically modifying donor neural cells such as porcine spinal cord cells, prior to implantation into a recipient subject. These methods include direct DNA uptake (transfection), and infection with viral vectors such as retrovirus, herpes virus, adenovirus, and adeno-associated virus vectors. Suhr, S. T. et al. 1993. *Arch. Neurol.* 50:1252. Transfection can be effected by endocytosis of precipitated DNA, fusion of liposomes containing DNA or electroporation. Suhr, S. T. et al. 1993. *Arch. Neurol.* 50:1252. Another method of transfecting donor cells is through the use of a "gene gun". In this method, microscopic DNA-coated particles are accelerated at high speeds through a focusing tube and "shot" or injected into cells in vitro (Klein, R. M. et al. 1992. *Biotechnology* 24:384; Zelenin, A. V. et al. 1989. *FEBS Lett.* 244:65) or in vivo (Zelenin, A. V. et al. 1991. *FEBS Lett.* 280:94)7. The cells close around the wound site and express genes carried into the cell on the particles.

Retroviral vectors typically offer the most efficient and best characterized means of introducing and expressing foreign genes in cells, particularly mammalian cells. These vectors have very broad host and cell type ranges, integrate by reasonably well understood mechanisms into random sites in the host genome, express genes stably and efficiently, and under most conditions do not kill or obviously damage their host cells. The methods of preparation of retroviral vectors have been reviewed extensively in the literature (Suhr, S. T. and Gage, F. H. 1993. *Arch Neurol.* 50:1252; Ray, J. and Gage, F. H. 1992. *Biotechniques* 13:598; Anderson, W. F. 1984. *Science* 226:401; Constantini, F. et al. 1986 *Science* 233:1192; Gilboa, E. et al. 1986. *Biotechniques* 4:504; Mann, R. et al. 1983. *Cell* 33:153; Miller, A. D. et al. 1985. *Mol. Cell Biol.* 5:431; and Readhead, C. et al. 1987 *Cell* 48:703) and are now in common use in many laboratories. Other techniques for producing genetically modified cells are described in detail in PCT publication WO 95/27042 and U.S. Pat. No. 5,082,670, the contents of which are incorporated herein by reference.

Culture of Neural Cells

The modified or unmodified cells described herein can be grown as a cell culture, i.e., as a population of cells which grow in vitro, in a medium suitable to support the culture (e.g., growth or stimulation) of the cells prior to administration to a subject. Media which can be used to support the growth of neural cells include mammalian cell culture media, such as those produced by Gibco BRL (Gaithersburg, Md.). See 1994 Gibco BRL Catalogue & Reference Guide. In addition, other substrates upon which the neural cells can grow including, for example, collagen, collagen plus polyomithine and poly-omithine plus fibronectin, can be used. The medium can be serum-free or supplemented with animal serum such as fetal calf serum. Moreover, growth factors, e.g., neurotrophic factors, can be added to the cell culture to promote neural cell growth in vitro. Examples of neurotrophic factors include glial cell line-derived growth factor, brain-derived neurotrophic factor, platelet-derived growth factor, neural growth factor, ciliary neurotrophic factor, midkine, insulin-like growth factor I and II, insulin, fibroblast growth factor, neurotrophin-3, neurotrophin 4/5 and transforming growth factor β

Methods of Treating Chronic Pain and/or Spasticity

Modified or unmodified neural cells can be administered to a subject with or without additional agents to treat chronic pain and/or spasticity. As used herein, the terms "introducing", "implanting", "delivering", "administering", and "transplanting" are used interchangeably. The neural cells of the invention are administered to a subject by any appropriate route which results in delivery of the cells to a desired location in the subject. In preferred embodiments, the cells are administered to the spinal cord of the subject. Cells can be delivered into the spinal cord of a subject e.g., by direct stereotaxic injection of the cells. In more preferred embodiments, the cells are administered into the spinal dorsal horn of the spinal cord or are administered to the subarachnoid space around the spinal cord (the space surrounding the spinal cord (between the arachnoidea and pia mater) that is filled with cerebral spinal fluid) using methods that are known in the art (see e.g., Eaton et al. 1997. *Pain.* 72:59; Sagen and Pappas. 1987. *Ann N Y Acad Sci.* 495: 306; or Ibuki et al. 1997. *Neuroscience* 76:845).

Cells can be administered in a physiologically compatible carrier, such as a buffered saline solution.

The cells of the invention can be inserted into a delivery device which facilitates introduction by e.g., injection, of the cells into the subjects. Such delivery devices include tubes, e.g., catheters, for injecting cells and fluids into the body of a recipient subject. In a preferred embodiment, the cells of the invention can be introduced into the subject at a desired location using a micropipette. The neural cells of the invention can be inserted into such a delivery device, e.g., a micropipette or syringe, in the form of a solution, e.g., a cell suspension. Alternatively, the cells can be embedded in a support matrix when contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosol, and the like. Solutions of the invention can be prepared by using a pharmaceutically acceptable carrier or diluent and, as required, other ingredients enumerated above, followed by filtered sterilization, and then incorporating porcine neural cells as described herein.

Support matrices in which the neural cells can be incorporated or embedded include matrices which are recipient-compatible and which degrade into products which are not harmful to the recipient. Natural and/or synthetic biodegradable matrices are examples of such matrices. Natural biodegradable matrices include collagen matrices. Synthetic biodegradable matrices include synthetic polymers such as polyanhydrides, polyorthoesters, and polylactic acid. A preferred support matrix for use in the present invention is gelfoam (Upjohn Kalamazoo, Mich.). In addition, the cells of the invention can be administered in a guidance channel (e.g., polyacrylonitrile/polyvinylchloride (PAN/PVC) guidance channels), such as those described in Bunge et al. 1994. *J Neurology* 241:536, which can serve as a guide for regenerating axons.

Use of Additional Agents

The cells of the present invention can be incubated and/or treated at any stage in their preparation for transplantation, e.g., during dissection, limited digestion, dissociation, plating, and/or production of cell suspensions for transplantation, with a number of agents or factors e.g., which promote the survival, growth, differentiation, and/or integration of the cells in vitro and/or in the recipient subject, or which further aid in the treatment of chronic pain and/or spasticity. The administration of additional agents can begin prior to transplantation of cells, can begin at the time of transplantation, or can begin after transplantation. The administration of additional agents can be limited in duration (e.g., can consist of a single administration of the agent) or can be of prolonged duration (e.g., can be given to the subject repeatedly over a long period of time).

In one embodiment, such agents or factors can be added at the site of transplantation in the recipient subject after the cells of the invention have been transplanted therein. In some instances, these agents can, for example, minimize or counteract detrimental effects on the cells resulting from the procedures used to prepare the cells for transplantation. For example, cells, when isolated from the donor pigs and prepared for transplantation, may experience cellular trauma and/or hypoxia which lead to the production of reactive oxygen species (ROS) such as superoxide radical anion, hydrogen peroxide, and the hydroxyl free radical. Colton, C. A. et al. 1995. *Exp. Neurol.* 132:54. ROS are known to adversely affect neural function, most likely by affecting a variety of membrane and intracellular components including ion channels, membrane lipids, transport mechanisms such as the Na+/K+ ATPase and Na+/glutamate exchange transport and cytosolic enzymes such as glutamine synthase. Colton, C. A. et al. 1995. *Exp. Neurol.* 132:54. Acute exposure of nerve terminals to ROS results in failure of neurotransmission. Colton, C. A. et al. 1991. *Free Rad. Res. Commun.* 14:385; Colton, C. A. et al. 1989. *Free Rad. BioL Med.* 7:3–8. Long term exposure of nerve terminals to ROS results in retraction of neurites and eventually, neuronal death. Halliwell, B. et al. Free Radicals in Biology and Medicine, 2nd ed. (Clarendon Press, Oxford, England 1989). In addition, it is known that ROS provoke membrane lipid peroxidation, consequently reducing the survival of neural cells in the transplants.

To minimize and/or counteract the adverse effects of these types of oxidative stress during preparation for transplantation, the cells of the present invention can be incubated and/or treated with antioxidants at any stage during the preparation. Examples of such antioxidants include the enzyme antioxidants superoxide dismutase (SOD) and glutathione peroxidase (Colton, C. A. et al. 1995. *Exp. Neurol.* 132:54) which are commercially available from Boehringer Mannheim (Indianapolis, Ind.) and Sigma Chemical Company (St. Louis, Mo.), respectively, agents which promote glutathione formation, e.g. N-acetyl cysteine (NAC), also commercially available from Sigma, and other known antioxidants such as lazaroids, e.g., U-74389G and U-83836E, which are available from Upjohn (Nakao, N. et al. 1994 *Proc. Natl. Acad. Sci. USA* 91:12408; Frodl, E. M. et al. 1994. *NeuroReport* 5:2393). Antioxidant enzymes, such as SOD, scavenge ROS and prevent the reaction of superoxide with nitric oxide to form peroxynitrite anion, which has been shown to be toxic to cultured neurons. Nakao, N. et al. 1995 *Nature Medicine* 1:226. These enzymes can be incubated with the cells of the invention as described above. Another method of introducing these enzymes into the cellular preparations of the present invention is to genetically modify the cells to contain the nucleic acid encoding such enzymes. The genetically modified cells can then produce agents which enhance the survival, growth, and differentiation of the grafted cells in the recipient subject. For example, porcine cells of the invention can be transfected with the human gene for Cu/Zn superoxide dismutase, a pivotal enzyme in the detoxification of oxygen free radicals, Nakao, N. et al. 1995. *Nature Medicine* 1:226). These transfected cells then express SOD and, consequently, efficiently detoxify ROS generated during tissue preparation and implantation to thereby increase graft survival.

Lazaroids are 21-aminosteroids that lack glucocorticoid activity and are specifically designed to localize within cell membranes and inhibit lipid peroxidation (stabilize membranes by inserting their lipophilic portion into the phospholipid bilayer (Nakao, N. et al. 1994. *Proc. Natl. Acad.*

Sci. USA 91:12408; Frodl, E. M. et al. 1994. NeuroReport 5:2393). Lazaroids are also known to scavenge free radicals, in particular, hydroxyl radicals. Other examples of antioxidants which can be added to the cell cultures and cell suspensions include TGFβ (Prehn, J. H. M et al. 1994. Proc. Natl. Acad. Sci. USA 91:12599), vitamin E (Nakao, N. et al. 1995. Nature Medicine 1:226), vitamin C, beta carotene, and other compounds which scavenge ROS, inhibit the production of ROS, and/or inhibit lipid peroxidation.

In addition, the oxidative environment of the cells in vitro can be modified to inhibit cellular oxidative stress. For example, during preparation of the cells for transplantation, the partial pressure of oxygen in the cells' environment can be decreased from the normal oxygen partial pressure, i.e., approximately 150 torr $O_2$, to a decreased oxygen partial pressure, i.e., 38 torr $O_2$ (about 5% $O_2$). This method of decreasing oxidative stress can be combined with treatment of the cells with one or more of the above-described antioxidants. For example, the combination of the partial oxygen pressure of 38 torr (e.g., 5% $O_2$) and treatment with NAC is effective for promoting survival of TH+ neurons. Colton, C. A. et al. 1995. Exp. Neurol. 132:54.

During the hypoxic conditions associated with the preparation of the cells of the invention for transplantation, the release of excitatory amino acids in the extracellular space stimulates N-methyl-D-aspartate (NMDA) receptors to increase the activity of nitric oxide synthase (NOS) which in turn results in increased biosynthesis of nitric oxide (NO). Nitric oxide is a neurotransmitter which can be toxic under conditions of excessive formation. Dawson, T. et al. 1995. The Neuroscientist 1:7. The toxic effects of NO occur through an interaction with the superoxide anion to form peroxynitrite, a highly reactive molecule which is able to nitrosylate proteins as well as initiate lipid peroxidation. Peroxynitrite also spontaneously decomposes to the hydroxyl and $NO_2$ free radicals, which mediate a variety of toxic effects. Dawson, T. et al. 1995 The Neuroscientist 1:7. Inhibitors of NOS, such as gangliosides, FK506, and cyclosporine A (Dawson, T. et al. 1995. The Neuroscientist 1:7), can be added to the cell preparations to inhibit the production of NO, thereby decreasing the production of peroxynitrite and its derivatives. Superoxide dismutase is another agent which can decrease the adverse effects of overproduction of NO and the toxic effects it mediates. Dawson, T. et al. 1995. The Neuroscientist 1:7.

Trauma and its associated adverse effects, e.g., membrane peroxidation, free radical induced cell damage (González-Garcia, M. et al. 1995. Proc. Natl. Acad. Sci. USA 92:4304; Zhong, L -T. et al. 1993. Proc. Natl. Acad. Sci. USA 90:4533), induced by preparation of the cells of the invention for implantation can also result in programmed cell death (apoptosis) of the transplanted cells. To reduce the occurrence of apoptosis in the transplanted cells, the cells of the invention can be transfected with nucleic acids encoding antiapoptotic gene products such as the bcl-2 (Talley, A. K. et al. 1995. Mol. Cell Biol. 15:2359; Merry, D. E. et al. 1994. Development 120:301; Prehn, J. H. et al. 1994. Proc. Natl. Acad. Sci. USA 91:12599; Zhong, L -T. et al. 1993. Proc. Natl. Acad. Sci. USA 90:4533), bcl-xL, the bcl-xβ (Gonzál\ez-Garcia, M. et al. 1995. Proc. Natl. Acad. Sci. USA 92:4304), and/or the crmA (Talley, A. K. et al. 1995. Mol. Cell Biol. 15:2359) gene product. These gene products have been shown to inhibit programmed neural cell death. In addition, the transfected cells of the invention can be treated with agents which unregulated the expression or function of these gene products, e.g., TGFβ1 and TGFβ3 which upregulate the expression of bcl-2 (González-Garcia, M. et al. 1995. Proc. Natl. Acad. Sci. USA 92:4304; Prehn, J. H. et al. 1994 Proc. Natl. Acad Sci. USA 91:12599) to augment the neuroprotective effect of the antiapoptotic gene products produced by the cells. Other factors, such as nerve growth factor (NGF) and platelet-derived growth factor (PDGF) have been found to have antiapoptotic activity (Zhong, L -T. et al. 1993 Proc. Natl. Acad. Sci. USA 90:4533). The cells of the invention, therefore, can also be transfected with nucleic acid encoding these factors. Enzyme antioxidants, such as superoxide dismutase and catalase (Bonfoco, E. et al. 1995 Proc. Natl. Acad. Sci. USA 92:7162), and other antioxidants, such as NAC (Talley, A. K. et al. 1995 Mol. Cell Biol. 15:2359) can also be used to prevent cells of the invention from undergoing programmed cell death during preparation for transplantation.

To further promote the survival of the cells of the invention in the recipient subject, the cells can be transplanted in conjunction with an angiogenic agent or transfected with nucleic acid encoding an angiogenic agent. Upon transplantation, the angiogenic agent promotes the ingrowth of blood vessels into the neural graft. As a result of this vessel ingrowth, the cells of the graft obtain sufficient nutrients to proliferate and survive within the recipient subject. Many growth factors exhibit angiogenic activity. For example, vascular endothelial growth factor (VEGF) (Drake, C. J. et al. 1995 Proc. Natl. Acad. Sci. USA 92:7657; Sharma, H. S. et al. 1995 Biochim. Biophys. Acta 1260:235; Millauer, B. et al. 1993. Cell 72:835), which occurs in four forms due to alternative splicing of its mRNA, is a potent endothelial mitogen. PDGF, acidic and basic fibroblast growth factor (FGF) (Drake, C. J. et al. 1995. Proc. Natl. Acad. Sci. USA 92:7657), epidermal growth factor (EGF), and K-FGF (Brüstle, O. et al. 1992. Oncogene 7:1177) also possess angiogenic activity and can be used in the methods of the invention to encourage blood vessel ingrowth into the transplanted cells of the invention.

Other factors, such as neurotrophic factors, which contribute to neural development, nerve fiber formation, and maintenance of neurons can be added to the cells of the invention in vitro during preparation for transplantation and/or to the cell suspension itself for introduction into the recipient subject along with the cells of the invention. The cells of the invention can also be genetically modified to produce such neurotrophic factors as described herein. The neurotrophic factor which is added to the cells of the present invention can be selected based on the presence of its receptors on the cells which are to be transplanted. For example, mesencephalic cells possess receptors for the following neurotrophic factors: glial cell line-derived neurotrophic factor (GDNF) (Tomac, A. et al. 1995 Nature 373:335; Beck, K. D. et al. 1995 Nature 373:339; Poulson, K. T. et al. 1994 Neuron 13:1245; Stromberg, I. et al. 1993 Exp. Neurol 124:401), which promotes the survival of, morphological differentiation of, and high affinity dopamine uptake in mesencephalic cells; brain-derived neurotrophic factor (BDNF) (Tomac, A. et al. 1995 Nature 373:335; Hyman, C. et al. 1994 J Neurotics. 14:335); ciliary neurotrophic factor (CNTF) (Hag, T. et al. 1993 Proc. Natl. Acad. Sci. USA 90:6315), which prevents axotomy induced degeneration of mesencephalic cells; midkine (Kikuchi, S. et al. 1993 Neurosci. Lett. 160:9), which promotes the survival and differentiation of mesencephalic cells; EGF (Casper, D. et al. 1991 J Neurosci. Res. 30:372; Knusel, B. et al. 1990 J Neurosci. 10:558), which increases survival and maturation of mesencephalic cells; insulin-like growth factor I and II and insulin (Knusel, B. et al. 1990 J Neurosci. 10:558); acidic FGF (Engele, J. et al. 1991 J. Neurosci. 11:3070);

basic FGF (Ferrari, G. et al. 1989 *Devel. Biol.* 133:140), which induce a significant increase in the number of neurite-bearing cells as well as in the degree of their fiber network; neurotrophin-3 (NT-3) and neurotrophin 4/5 (NT-4/5) (Hyman, C. et al. 1994. *J Neurosci.* 14:335-347); and transforming growth factor-$\beta$2 (TGF$\beta$2) and transforming growth factor-$\beta$3 (TGF$\beta$3) (Poulson, K. T. et al. 1994. *Neuron* 13:1245–1252).

Neurotrophic factors which promote the survival of neural cells can be selected based on the presence of receptors on the cells. Receptors for basic FGF (Ferrari, G. et al. 1989. *Devel. BioL* 133:140), BDNF (Hyman, C. et al. 1994 *J Neurosci.* 14:335), NT-3 and NT-4/5 (Hyman, C. et al. 1994 *J Neurosci.* 14:335) can be found on certain neural cells. Thus, in one embodiment, the cells of the invention can be transfected with the nucleic acids encoding one or more of these factors. In another embodiment, one or more of these factors can be added to the preparation of neural cells prior to transplantation. These neurotrophic factors enhance the survival of the cells of the invention in the recipient subject. Similarly, neurotrophic factors which exhibit specificity for cortical cells, and consequently, which can be used to promote the survival of such cell upon engraftment into a recipient subject, include nerve growth factor (NGF) (Lindsay, R. M. et al. 1994 *TINS* 17:182–190), which prevents, for example, atrophy of axotomized forebrain cholinergic neurons; BDNF, and NT-3 and NT-4/5 (Lindsay, R. M. et al. 1994. *TINS* 17:182–190').

In another embodiment, the neurotrophic factors described herein can be used together or in combination with other compounds, such as neurotransmitters, to augment their neurotrophic effects. For example, the combination of either acidic or basic FGF and a catecholamine, when contacted with the appropriate neural cells, simultaneously or sequentially, can induce tyrosine hydroxylase expression. Du, X. et al. 1995. *J Neurosci.* 15:5420. In addition, it is contemplated that various combinations of neurotrophic factors described herein can act synergistically and, therefore, can be used together to promote survival of the transplanted cells of the invention.

Certain drugs also possess neurotrophic activity. Examples of such drugs include FK506 and cyclosporin A (Lyons, W. E. et al. 1994. *Proc. Natl. Acad. Sci. USA* 91:3191; Steiner et al. 1997. *Nature Medicine* 3:421; Steiner et al. 1997. *Proc. Natl. Acad. Sci.* 94:2019) which block the neurotoxicity elicited by glutamate acting at N-methyl-D-aspartate (NMDA) receptors by, for example, augmenting phosphorylated levels of NOS. As phosphorylated NOS inhibits its catalytic activity, these drugs effectively reduce NO formation and prevent the neurotoxic effects of NMDA on these cells. Other drugs which possess neurotrophic activity and can be used in the present invention are those small molecules which bind to the same binding proteins as FK506 and/or cyclosporin A and, therefore, mediate similar neuroprotective effects. Lyons, W. E. et al. 1994 *Proc. Natl. Acad Sci. USA* 91:3191. In one embodiment, these drugs are administered to the subject in addition to the subject neural cells to treat chronic pain and/or spasticity.

In one embodiment, combinations of one or more of the above-described agents and factors can be used to promote survival of the cells of the invention prior to or after the cells are transplanted into recipient subjects. For example, cells of the present invention can be contacted with one or more of the agents or factors described herein to promote survival of the cells in vitro and/or in vivo. In another embodiment, the cells of the invention can be transfected with the nucleic acid of one or more of the agents or factors described herein and also contacted with one or more of the agents or factors described herein. Moreover, although many of the neurotrophic factors described herein are specific for a particular cell type, the association of these factors with such a cell type does not exclude the use of that factor with a different cell type. Treatment of the cells of the invention with the agents or factors described herein can occur simultaneously or sequentially.

In another embodiment, the administration of neural cells to treat chronic pain and/or spasticity can be coupled with administration of traditional therapies for these conditions (e.g., with opiods or baclofen). In certain subjects, such combination therapies may result in optimal amelioration of symptoms.

In another embodiment, agents which inhibit T cell activity in the subject can be administered in addition to the subject cells. As used herein, an agent which inhibits T cell activity is defined as an agent which results in removal (e.g., sequestration) or destruction of T cells within a subject or inhibits T cell functions within the subject (i.e., T cells may still be present in the subject but are in a non-functional state, such that they are unable to proliferate or elicit or perform effector functions, e.g. cytokine production, cytotoxicity etc.). The term "T cell" encompasses mature peripheral blood T lymphocytes. The agent which inhibits T cell activity may also inhibit the activity or maturation of immature T cells (e.g., thymocytes).

A preferred agent for use in inhibiting T cell activity in a recipient subject is an immunosuppressive drug. The term "immunosuppressive drug or agent" is intended to include pharmaceutical agents which inhibit or interfere with normal immune function. A preferred immunosuppressive drug is cyclosporin A. Other immunosuppressive drugs which can be used include FK506, and RS-61443. In another embodiment, an immunosuppressive drug is CellCept® (Available from Hoffmann-LaRoche Ltd., Basel, Switzerland). In one embodiment, the immunosuppressive drug is administered in conjunction with at least one other therapeutic agent. Additional therapeutic agents which can be administered include steroids (e.g., glucocorticoids such as prednisone, methyl prednisolone and dexamethasone) and chemotherapeutic agents (e.g., azathioprine and cyclosphosphamide). In a preferred embodiment, methyl-prednisolone is administered to the subject after transplantation of the cells of the invention such that local inflammatory responses are deterred. In another embodiment, an immunosuppressive drug is administered in conjunction with both a steroid and a chemotherapeutic agent. Suitable immunosuppressive drugs are commercially available (e.g., cyclosporin A is available from Novartis, Corp., East Hanover, N.J.).

An immunsuppressive drug is administered in a formulation which is compatible with the route of administration. Suitable routes of administration include intravenous injection (either as a single infusion, multiple infusions or as an intravenous drip over time), intraperitoneal injection, intramuscular injection and oral administration. For intravenous injection, the drug can be dissolved in a physiologically acceptable carrier or diluent (e.g., a buffered saline solution) which is sterile and allows for syringability. Dispersions of drugs can also be prepared in glycerol, liquid polyethylene glycols, and mixtures thereof and in oils. Convenient routes of administration and carriers for immunsuppressive drugs are known in the art. For example, cyclosporin A can be administered intravenously in a saline solution, or orally, intraperitoneally or intramuscularly in olive oil or other suitable carrier or diluent.

An immunosuppressive drug is administered to a recipient subject at a dosage sufficient to achieve the desired therapeutic effect (e.g., inhibition of rejection of transplanted cells). Dosage ranges for immunosuppressive drugs, and other agents which can be coadministered therewith (e.g., steroids and chemotherapeutic agents), are known in the art (See e.g., Freed et al. *New Engl. J Med.* 1992 327:1549: Spencer et al. 1992 *New Engl. J Med.* 327:1541; Widner et al. 1992. *New Engl. J Med.* 327:1556; Lindvall et al. 1992. *Ann. Neurol.* 31:155; and Lindvall et al. 1992. *Arch. Neurol.* 46:615). A preferred dosage range for immunosuppressive drugs, suitable for treatment of humans, is about 1–30 mg/kg of body weight per day. A preferred dosage range for cyclosporin A is about 1–10 mg/kg of body weight per day, more preferably about 1–5 mg/kg of body weight per day. Dosages can be adjusted to maintain an optimal level of the immunosuppressive drug in the blood of the recipient subject. For example, dosages can be adjusted to maintain a preferred serum level for cyclosporin A in a human subject of about 100–200 ng/ml. It is to be noted that dosage values may vary according to factors such as the disease state, age, sex, and weight of the individual. Dosage regimens may be adjusted over time to provide the optimum therapeutic response according to the individual need and the professional judgment of the person administering or supervising the administration of the compositions, and that the dosage ranges set forth herein are exemplary only and are not intended to limit the scope or practice of the claimed composition.

In one embodiment of the invention, an immunsuppressive drug is administered to a subject transiently for a sufficient time to induce tolerance to the transplanted cells in the subject. Transient administration of an immunosuppressive drug has been found to induce long-term graft-specific tolerance in a graft recipient (See Brunson et al. 1991. *Transplantation* 52:545; Hutchinson et al. 1981. *Transplantation* 32:210; Green et al. 1979. *Lancet* 2:123; Hall et al. 1985. *J Exp. Med.* 162:1683). Administration of the drug to the subject can begin prior to transplantation of the cells into the subject. For example, initiation of drug administration can be a few days (e.g., one to three days) before transplantation. Alternatively, drug administration can begin the day of transplantation or a few days (generally not more than three days) after transplantation. Administration of the drug is continued for sufficient time to induce donor cell-specific tolerance in the recipient such that donor cells will continue to be accepted by the recipient when drug administration ceases. For example, the drug can be administered for as short as three days or as long as three months following transplantation. Typically, the drug is administered for at least one week but not more than one month following transplantation. Induction of tolerance to the transplanted cells in a subject is indicated by the continued acceptance of the transplanted cells after administration of the immunosuppressive drug has ceased. Acceptance of transplanted tissue can be determined morphologically (e.g., with skin grafts by examining the transplanted tissue or by biopsy) or by assessment of the functional activity of the graft.

Another type of agent which can be used to inhibit T cell activity in a subject is an antibody, or fragment or derivative thereof, which depletes or sequesters T cells in a recipient. Antibodies which are capable of depleting or sequestering T cells in vivo when administered to a subject are known in the art. Typically, these antibodies bind to an antigen on the surface of a T cell. Polyclonal antisera can be used, for example anti-lymphocyte serum. Alternatively, one or more monoclonal antibodies can be used. Preferred T cell-depleting antibodies include monoclonal antibodies which bind to CD2, CD3, CD4 or CD8 on the surface of T cells. Antibodies which bind to these antigens are known in the art and are commercially available (e.g., from American Type Culture Collection). A preferred monoclonal antibody for binding to CD3 on human T cells is OKT3 (ATCC CRL 8001). The binding of an antibody to surface antigens on a T cell can facilitate sequestration of T cells in a subject and/or destruction of T cells in a subject by endogenous mechanisms. Alternatively, a T cell-depleting antibody which binds to an antigen on a T cell surface can be conjugated to a toxin (e.g., ricin) or other cytotoxic molecule (e.g., a radioactive isotope) to facilitate destruction of T cells upon binding of the antibody to the T cells. See PCT publication WO 95/26740, for further details concerning the generation of antibodies which can be used in the present invention.

Another type of antibody which can be used to inhibit T cell activity in a recipient subject is an antibody which inhibits T cell proliferation. For example, an antibody directed against a T cell growth factor, such as IL-2, or a T cell growth factor receptor, such as the IL-2 receptor, can inhibit proliferation of T cells (See e.g., DeSilva, D. R. et al. 1991. *J Immunol.* 147:3261-3267). Accordingly, an IL-2 or an IL-2 receptor antibody can be administered to a recipient to inhibit rejection of a transplanted cell (see e.g. Wood et al. 1992. *Neuroscience* 49:410). Additionally, both an IL-2 and an IL-2 receptor antibody can be coadministered to inhibit T cell activity or can be administered with another antibody (e.g., which binds to a surface antigen on T cells).

An antibody which depletes, sequesters or inhibits T cells within a recipient can be administered at a dose and for an appropriate time to inhibit rejection of cells upon transplantation. Antibodies are preferably administered intravenously in a pharmaceutically acceptable carrier or diluent (e.g., a sterile saline solution). Antibody administration can begin prior to transplantation (e.g., one to five days prior to transplantation) and can continue on a daily basis after transplantation to achieve the desired effect (e.g., up to fourteen days after transplantation). A preferred dosage range for administration of an antibody to a human subject is about 0.1–0.3 mg/kg of body weight per day. Alternatively, a single high dose of antibody (e.g., a bolus at a dosage of about 10 mg/kg of body weight) can be administered to a human subject on the day of transplantation. The effectiveness of antibody treatment in depleting T cells from the peripheral blood can be determined by comparing T cell counts in blood samples taken from the subject before and after antibody treatment. Dosage regimes may be adjusted over time to provide the optimum therapeutic response according to the individual need and the professional judgment of the person administering or supervising the administration of the compositions. Dosage ranges set forth herein are exemplary only and are not intended to limit the scope or practice of the claimed composition.

The present invention is further illustrated by the following examples which in no way should be construed as being further limiting. The contents of all cited references (including literature references, issued patents, published patent applications, and co-pending patent applications) cited throughout this application are incorporated herein by reference.

EXAMPLES

Example 1

Treatment of Chronic Constriction Injury in Rats

Chronic constriction injury (CCI) has been used as a model to test the ability of transplants to relive pain-related behaviors (Hama and Sagen. 1994. *Pain.* 52:223). The peripheral neuropathy model of chronic pain developed by Bennett and Xie. 1988. *Pain* 33:87) has been adopted and extensively studied by many laboratories. The Bennett model produces abnormal pain sensations by loose constrictive ligatures (4-0 chromic gut suture) tied around the rat's sciatic nerve. These ligatures evoke intraneural edema, the swelling is opposed by ligatures and the nerve strangulates (Bennett, 1993. *Muscle and Nerve.* 16:1040). This model is often referred to as the chronic constriction injury model (CCI), because the nerve is constricted for at least 30 days. The predominant effect is a massive degeneration of large myelinated fibers (A$\beta$) distal to the constriction with a distinctly less severe effect on small myelinated fibers (A$\delta$) and unmyelinated C-fibers (Munger et al., 1992. *Exp. NeuroL* 118:204).

Examples of behavioral tests which can be performed to assess pain sensitivity following CCI include: cold allodynia (the response to cold stimuli), thermal hyperalgesia (the response to heat stimuli), and mechanical allodynia (the response to normally innocuous mechanical stimuli, e.g., von Frey hairs) (Eaton et al. 1997. *Pain.* 72:59).

Fetal Porcine Cell Isolation

Donor gilts for research purposes were procured from Parson's Farm (Hadley, Mass.) or Tufts University School of Veterinary Medicine where timed pregnancies were obtained by natural breeding or artificial insemination. Fetal lateral ganglionic eminence (LGE) tissue was dissected from the ventrolateral wall of the lateral ventricle (Pakzaban et al. 1995. *Neuroscience* 65, 938–996.). LGE tissue from 8–12 fetuses was minced, and pooled. The fetal tissue was incubated with 0.5% Trypsin-EDTA in Hanks balanced salt solution (HBSS). To facilitate dissociation, the tissue was washed in the presence of DNase (final concentration 50 $\mu$g/ml). Following washing, the tissue was triturated in the presence of DNase by passing it through fire polished Pasteur pipettes with decreasing bore size until a single cell suspension was attained. The cells were washed and re-suspended in the appropriate media for transplantation at a concentration of approximately 100,000 cells per microliter.

Prior to transplantation approximately half of the obtained LGE cells were immunomodulated with an anti-MHC Class I F(ab')$_2$ fragment to prevent rejection. Cells were resuspended to 1×10$^7$ cells per ml in HBSS containing 10 $\mu$g per ml anti-MHC Class I F(ab')$_2$ fragment (PT85, Veterinary Medicine Research and Development Inc.). Following a 1 hour incubation period, the cells were rinsed to remove unbound F(ab')$_2$ fragment and resuspended in Transplantation Media.

Animals and Experimental Design 13 female (200–235 g starting weight) Sprague-Dawley (Taconic Farms) were used in this study. Experimental design consisted of 2 treatment groups: 7 animals received transplanted porcine LGE cells and were immunosuppressed with daily injections of Cylcosporin A (15 mg/kg, s.c.), 6 immunosuppressed rats received a control saline transplant. The weight of all of the animals in the study over time (at the initiation of the study (baseline), post CCI injury (CCI), and post transplant (post tp) )was comparable (FIG. 1).

Transplantation Surgery

Intraspinal transplantation was achieved by using methods previously described (Reier et al. 1986. *J Comp. Neurol.* 247:275–296; Stokes, B. T. and Reier, P. J. 1992. *Exp. Neurol.* 116:1–12). Rats were anesthetized with ketamine (87 mg/ml) and zylazine (13 mg/ml) for all surgical procedures. Several spinal segments (T12-L2) of the spinal cord were exposed via drilling or laminectomy and the cord was immobilized on a frame to ensure stereotaxic implantation. Engraftment was accomplished by injecting 1 $\mu$l of 1×10$^5$ cells through a glass micropipette attached to a 1 $\mu$l Hamilton syringe into the intact lumbar spinal cord. The pulled micropipettes have an outside diameter of 50–100 $\mu$m, thus increasing the accuracy of delivering cells to small targets and decreasing the damage caused by the needle. Two discrete deposits of 0.5 $\mu$l of either saline or 0.5×10$^5$ cells of porcine cells were injected each over a one minute period within the same needle track at the following coordinates relative to the dorsal spinal artery: lateral –0.7 mm; ventral –0.7 mm and –0.5 mm. There was a one minute wait between injections. In addition, the glass tip remained in the spinal cord for 5 minutes following the –0.5 mm injection to prevent back flow out of LGE cells upon removal of the micropipette tip. The musculature was sutured (3-0 ethicon), and the skin closed with autoclips.

Behavioral Assessment of Sensory Processing

Figure 2:
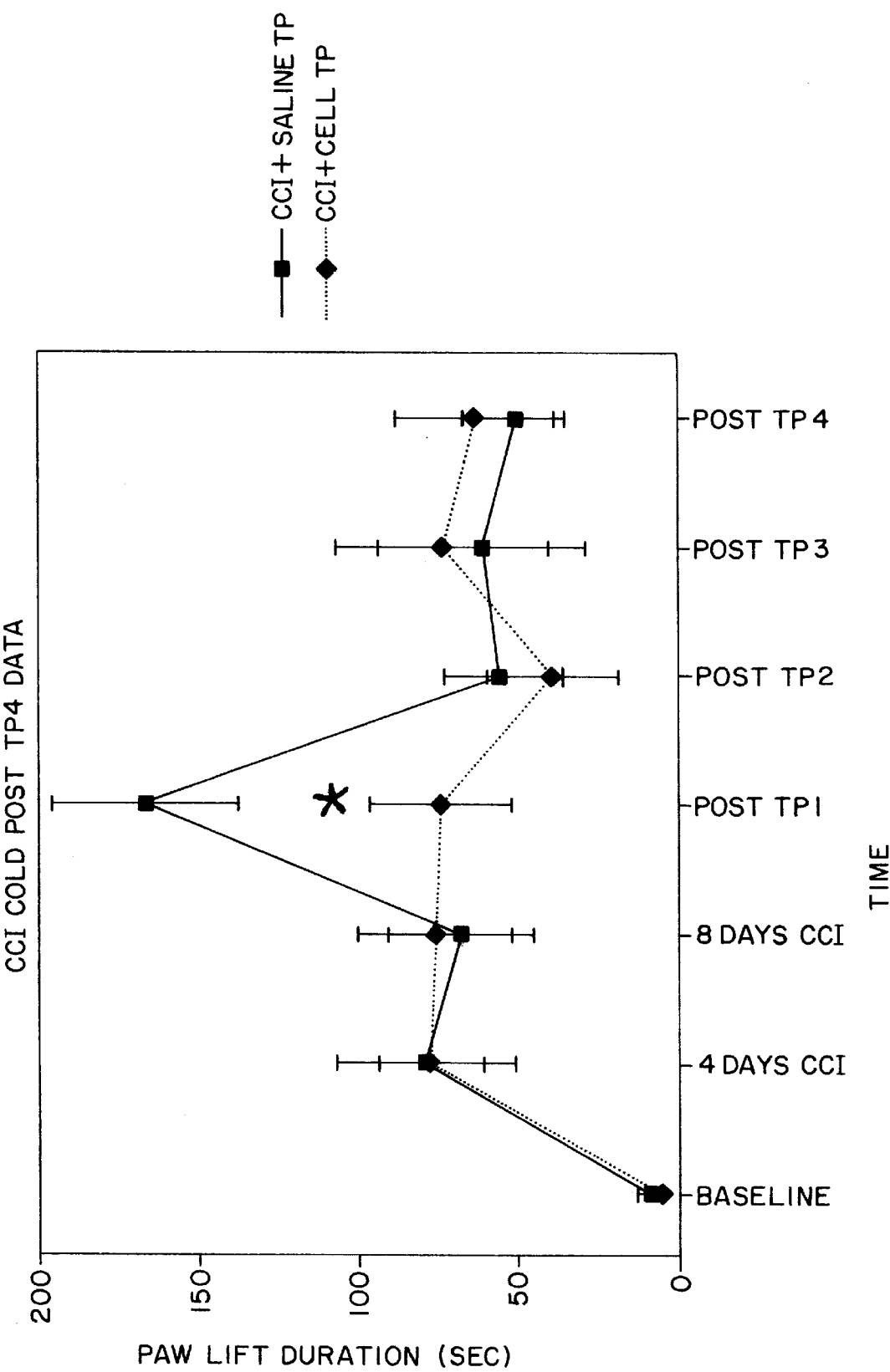
FIG. 2 is a graph depicting animals that received neural cells (open diamonds) showed a reduction in abnormal response to cold as demonstrated by lower paw lift duration using this test.
Figure 3:
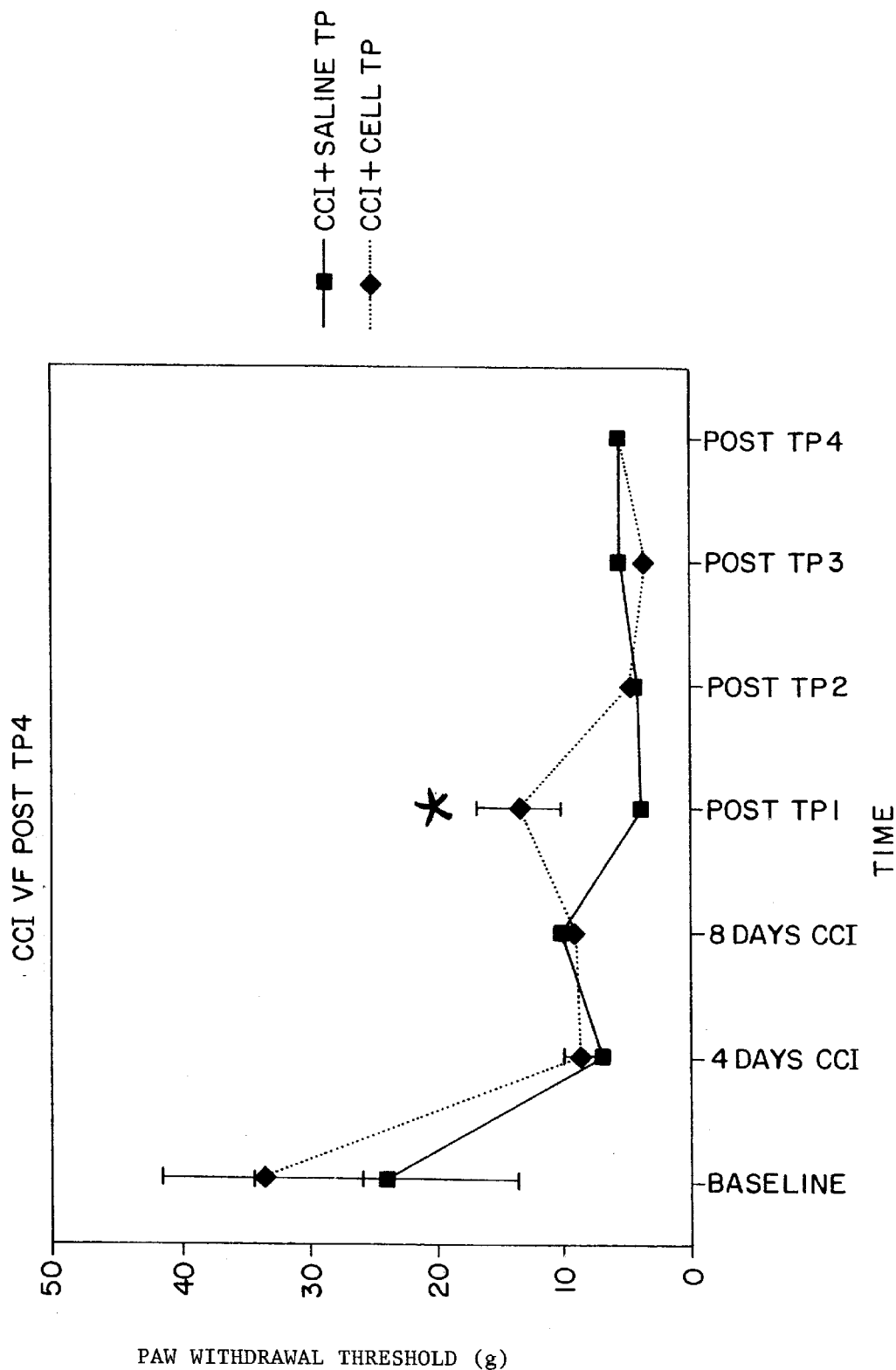
FIG. 3 is a graph depicting animals that received neural cells (open diamonds) showed a reduced sensitivity to mechanical stimuli (calibrated von Frey hairs) as measured by higher paw withdrawal threshold using this test.
Figure 4:
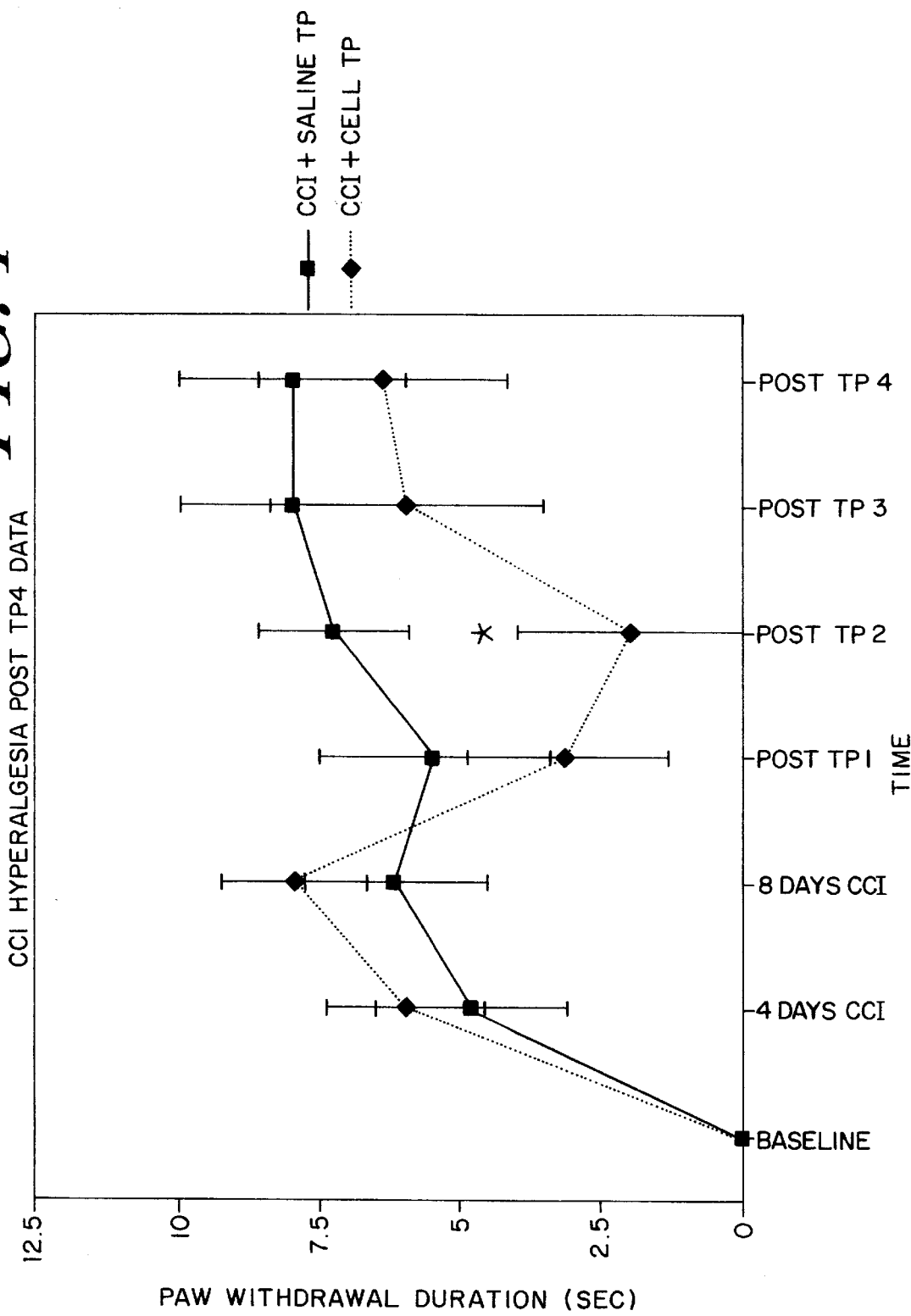
FIG. 4 is a graph depicting that animals that received neural cells (open diamonds) had decreased paw withdrawal duration to mechanical stimulation (a single prick) than animals that received saline using this test.

Animals were allowed to recover from surgical procedures for one week prior to commencement of behavioral testing. Observation of behavior was conducted over time (at the initiation of the study (baseline), post CCI injury (CCI), and post transplant (post tp)). Responses to noxious and innocuous stimuli were determined using three tests sequentially: a copper plate chilled over ice to 4° C. for cold allodynia, von Frey thresholds for tactile allodynia, and a pin prick test for mechanical hyperalgesia. To assess abnormal response to the cold, rats were placed in a clear plexi-glass box upon a copper plate chilled to 4° C. Testing was monitored for 5 minutes. The duration of paw(s) lifts was recorded during the testing period. FIG. 2 shows that animals which received neural cells (open diamonds) showed a reduced sensitivity to pain as demonstrated by lower paw lift duration using this test (statistical significance is indicated by the asterisk). For assessment of tactile allodynia, a series of calibrated von Frey hairs, ranging from 3.6–75.9 g were used. Animals were placed on an elevated plastic grafted surface and von Frey hairs were indented on the hind paw mid-plantar skin until they just bent 5 times at a frequency of approximately 2/sec (Seltzer et al. 1991. *Pain* 45, 69–75.). Testing was alternated between both hind paws until withdrawal threshold was reached (average of both sides). FIG. 3 shows that animals that received neural cells (open diamonds) showed a reduced sensitivity to pain as measured by higher paw withdrawal threshold using this test (statistical significance is indicated by the asterisk). To assess mechanical hyperalgesia, a single prick was applied to the mid plantar glabrous surface of each hind paw. Responses were recorded as duration for which the paw(s) was raised (Seltzer, et al. 1990. *Pain* 43, 205–218.). FIG. 4 shows that animals that received neural cells (open diamonds) had lowered paw withdrawal duration than animals that received saline using this test (statistical significance is indicated by the asterisk).

Behavioral Assessment of Motor Integration

Locomotion was assessed using the Basso, Beattie, and Beshnahan (Basso et al. 1996. *Journal of Neurotrauma.* 13:343; Basso et al. 1996. *Experimental Neurology* 139:244) modified locomotion open field test. In this test, rats were given scores based upon their locomotion ability. The scale ranges from 0 to 21, where 0 is no hind limb movement, and 21 produces normal gait responses and free easy movement, with appropriate paw placement. FIG. 5 shows that all of the animals in the study showed normal behavior using this test.

The ability of a rat to transverse a widely spaced wire mesh (4×4 cm spaces) was determined. The ability to grasp the wire during walking was observed. A positive reflex occurs as a grasping response when the hind paws contacted and grasped the wires. Normal rats should show this reflex with every step as they transverse the grid. The ability of rats to cross 5 open squares on the grid was scored. An uninjured rat should receive a score of 5 on the grid walking test, which translates to 5 successful grasps on 5 open squares (Siegan, J. B., and Sagen, J. 1997. *Pharmacol. Biochem. Behav.* 58, 1–8.). FIG. 5 shows that all of the animals in the study showed normal behavior (N) using this test.

The ability for a rat to transverse an elevated beam (1.5 m×4.7 cm) was assessed. Incorporation of both supraspinal and propiospinal pathways were utilized to facilitate correct placement of all four limbs and allow the rat to maintain postural balance. The ability of the animal to cross the beam was scored according a 5 point scale where 5 is normal. FIG. 5 shows that all of the animals in the study showed normal behavior using this test.

Histological Procedures

Animals were sacrified 4 weeks following transplantation of LGE cells or saline. Transcardial perfusion was performed on each animal with .9% heparinized saline followed by Zamboni's fixative. Spinal cords were post-fixed for 24 hours in the vertebral column prior to identification and removal of the transplanted area. Spinal cord tissue was paraffin embedded and seconded at 5–7 $\mu$m. Serial sections were stained with hematoxylin and eosin to appropriately identify the transplanted area prior to performing additional immunohistochemistry.

Selected spinal cord sections were deparaffinized and analyzed for porcine cells with a pig repetitive DNA sequence as a probe, porcine cell nuclei were detected by in situ hybridization as previously described (Deacon, et al. 1997. *Nat. Med.* 3:350; Galpern, et al. 1996. *Exp. Neurol.* 140: 1). In this way, LGE cells have been visualized in the splina cords of recipient animals, thus confirming that LGE cells transplanted into the intact rat spinal cord were not of host origin and that these cells survived in the host animals.

Example 2

Methods of Detecting Pathogens in Swine

A. Collecting, processing, and analyzing pig samples for signs of pathogens

For detecting pathogens in swine samples can be taken from any source, e.g., blood, serum, urine, feces, or tissue, as appropriate for the particular pathogen to be detected. Appropriate samples to take for detection of a given pathogen and means of detection pathogens are known in the art and include, e.g., serological assays, identification of pathogen genetic material (e.g., by PCR), and/or culture of pathogens.

In one example, feces are extracted from the pig's rectum manually and placed in a sterile container. About a 1.5 cm diameter portion of the specimen was mixed thoroughly in 10 ml of 0.85% saline. The mixture is then strained slowly through a wire mesh strainer into a 15 ml conical centrifuge tube and centrifuged at 650×g for 2 minutes to sediment the remaining fecal material. The supernatant is decanted carefully so as not to dislodge the sediment and 10% buffered formalin was added to the 9 ml mark, followed by thorough mixing. The mixture is allowed to stand for 5 minutes. 4 ml of ethyl acetate is added to the mixture and the mixture is capped and mixed vigorously in an inverted position for 30 seconds. The cap is then removed to allow for ventilation and then replaced. The mixture is centrifuged at 500×g for 1 minute (four layers should result: ethyl acetate, debris plug, formalin and sediment). The debris plug is rimmed using an applicator stick. The top three layers are carefully discarded by pouring them off into a solvent container. The debris attached to the sides of the tube is removed using a cotton applicator swab. The sediment is mixed in either a drop of formalin or the small amount of formalin which remains in the tube after decanting. Two separate drops are placed on a slide to which a drop of Lugol's iodine is added. Both drops are coverslipped and carefully examined for signs of pathogens, e.g., protozoan cysts of trophozoites, helminth eggs and larvae. Protozoan cyst identification is confirmed, when required, by trichrome staining.

B. Co-cultivation assay for detecting the presence of human and animal viruses in pig cells Materials Cell Lines African green monkey kidney, (VERO), cell line American Type Culture Collection, (ATCC CCL81), human embryonic lung fibroblasts, (MRC-5) cell line American Type Culture Collection, (ATCC CCL 171), porcine kidney, (PK-15), cell line American Type Culture Collection, (ATCC CRL 33), porcine fetal testis, (ST), cell line American Type Culture Collection, (ATCC CRL 1746)

Medium Antibiotics, and Other Cells, and Equipment

Fetal calf serum, DMEM, Penicillin 10,000 units/ml, Streptomycin 10 mg/ml, Gentamicin 50 mg/ml, guinea pig erythrocytes, chicken erythrocytes, porcine erythrocytes, Negative Control (sterile cell culture medium), Positive Controls: VERO and MRC-5 Cells: Poliovirus type 1 attenuated, (ATCC VR-1 92) and Measles virus, Edmonston strain, (ATCC VR-24), PK-1 5 and ST Cells: Swine influenza type A, (ATCC VR-99), Porcine Parvovirus, (ATCC VR-742), and Transmissible gastroenteritis of swine, (ATCC VR-743). Equipment: tissue Culture Incubator, Inverted Microscope, Biological Safety Cabinet.

These materials can be used in a co-cultivation assay (a process whereby a test article is inoculated into cell lines (VERO, MRC-5, PK1 5, and ST) capable of detecting a broad range of human, porcine and other animal viruses). Hsuing, G. D., "Points to Consider in the Characterization of Cell Lines Used to Produce Biologicals" in Diagnostic Virology, 1982 (Yale University Press, New Haven, Conn., 1982).

Experimental Design and Methodology

A total of three flasks (T25) of each cell line are inoculated with at least 1 ml of test article. Three flasks of each cell line can also be inoculated with the appropriate sterile cell culture medium as a negative control. Positive control viruses are inoculated into three flasks of each cell line. After an absorption period, the inoculate is removed and all flasks incubated at 35–37° C. for 21 days. All flasks are observed at least three times per week for the development of cytopathic effects, (CPE), of viral origin. Harvests are made from any flasks inoculated with the test article that show viral CPE.

At Day 7 an aliquot of supernatant and cells from the flasks of each test article are collected and at least 1 ml is inoculated into each of three new flasks of each cell line. These subcultures are incubated at 35–37° C. for at least 14 days. All flasks are observed and tested as described above.

At Day 7, the flasks from each test article are also tested for viral hemadsorption, (HAd), using guinea pig, monkey and chicken erythrocytes at 2–8° C. and 35–37° C. at 14 days postinoculation.

At Day 21, if no CPE is noted, an aliquot of supernatant from each flask is collected, pooled, and tested for viral hemagglutination, (HA), using guinea pig, monkey, and chicken erythrocytes at 2–8° C. and 35–37° C. Viral identification is based on characteristic viral cytopathic effects (CPE) and reactivity in HA and HAd testing.

The test samples are observed for viral cytopathic effects in the following manner: All cultures are observed for viral CPE at least three times each week for a minimum of 21 days incubation. Cultures are removed from the incubator and observed using an inverted microscope using at least 40× magnification. 100× or 200× magnification is used as appropriate. If any abnormalities in the cell monolayers, including viral CPE, are noted or any test articles cause total destruction of the cell monolayer, supernatant and cells are collected from the flasks and samples are subcultured in additional flasks of the same cell line. Samples can be stored at −60° to −80° C. until subcultured. After 7 and 14 days incubation, two blind passages are made of each test article by collecting supernatant and cells from all flasks inoculated with each sample. Samples can be stored at −60° to −80° C. until subcultured.

Hemadsorbing viruses are detected by the following procedure: after 21 days of incubation, a hemadsorption test is performed to detect the presence of hemadsorbing viruses. Supernatant fluids are collected and pooled from each flask inoculated with test articles or controls. Fluids are tested using guinea pig, monkey, and chicken erythrocytes. Hemagglutination testing is also performed after 21 days of incubation of the subcultures. Viral isolates are identified based on the cell line where growth was noted, the characteristics of the viral CPE, the hemadsorption reaction, and hemagglutination reactions, as appropriate. The test article is considered negative for the presence of a viral agent, if any of the cell lines used in the study demonstrate viral, CPE, HA, or HAd in a valid assay.

C. Procedure for preparing and maintaining cell lines used to detect viruses in pig cells Materials Fetal calf serum (FCS), DMEM, Penicillin 10,000 unit/ml, Streptomycin 10 mg/ml, Gentamicin 50 mg/ml, T25 tissue culture flasks, tissue culture incubator (5% $CO_2$, 37° C.)

Procedure

Aseptic techniques are followed when performing inoculations and transfers. All inoculations and transfers are performed in a biological safety cabinet. Media is prepared by adding 10% FCS for initial seeding, 5% FCS for maintenance of cultures, as well as 5.0 ml of penicillin/streptomycin and 0.5 ml of gentamicin per 500 ml media. Sufficient media is added to cover the bottom of a T25 tissue culture flask. The flask is seeded with the desired cell line and incubated at 37° C., 5% $CO_2$ until cells are 80 to 100% confluent. The flasks are then inoculated with virus (QCP25).

D. Preparation of erythrocyte (rbc) suspensions used in hemadsorption (HAd) and hemagglutination (HA) virus detection testing Materials Phosphate buffered saline, (PBS), pH 7.2, guinea pig erythrocytes stock solution, porcine erythrocytes stock solution, chicken erythrocytes stock solution, sterile, disposable centrifuge tubes, 15 or 50 ml Laboratory centrifuge Procedure An appropriate amount of erythrocytes (rbc) is obtained from stock solution. The erythrocytes are washed 3 times with PBS by centrifugation at approximately 1000×g for 10 minutes. A 10% suspension is prepared by adding 9 parts of PBS to each one part of packed erythrocytes. The 10% rcb suspensions are stored at 2–8° C. for no more than one week. 0.5% ecb suspensions are prepared by adding 19 parts of PBS to each one part of 10% rbc suspension. Fresh 0.5% rbc suspensions are prepared prior to each day's testing.

Hemagglutination (HA) test

A hemagglutination test is a test that detects viruses with the property to agglutinate erythrocytes, such as swine influenza type A, parainfluenza, and encephalomyocarditis viruses, in the test article. Hsuing, G. D. 1982. Diagnostic Virology (Yale University Press, New Haven, Conn.);. Stites, Daniel P and Terr, Abba I, 1991, Basic and Clinical Immunology (Appleton & Lange, East Norwalk, Conn.).

Materials

Supernatants from flasks of the VERO cell line, MRC-5 inoculated with the test article, flasks of positive and negative controls, phosphate buffered saline (PBS), pH 7.2, guinea pig erythrocytes (GPRBC), 0.5% suspension in PBS, chicken erythrocytes (CRBC), 0.5% suspension in PBS, porcine erythrocytes (MRBC), 0.5% suspension in PBS Procedure All sample collection and testing is performed in an approved biological safety cabinet. 0.5% suspensions of each type of erythrocytes are prepared as described above. The HA test on all cell lines inoculated with samples of the test articles at least 14 days post-inoculation. Positive and negative control cultures are included for each sample and monolayers are examined to ensure that they are intact prior to collecting samples.

At least 1 ml of culture fluid from each flask inoculated with the test article is collected and pooled. 1 ml samples from the negative and positive control cultures are also collected and pooled. A set of tubes is labeled with the sample number and type of erythrocyte (distinguish positive and negative suspension) to be added. Racks may be labeled to differentiate the type of erythrocyte. 0.1 ml of sample is added to each tube. 0.1 ml of the appropriate erythrocyte suspension is added to each tube. Each tube is covered with parafilm and mixed thoroughly. One set of tubes is incubated at 2–8° C. until tight buttons form in the negative control in about 30–60 minutes. Another set of tubes is incubated at 35–37° C. until tight buttons form in the negative control in about 30–60 minutes.

Formation of a tight button of erythrocytes indicates a negative result. A coating of the bottom of the tube with the erythrocytes indicates a positive result.

E. Methods used for fluorescent antibody stain of cell suspensions obtained from flasks used in detection of viruses in porcine cells using cell culture techniques (as described in Sections B and C)

Materials

Pseudorabies, parvovirus, enterovirus. adenovirus, transmissible Gastroenteritis Virus. bovine viral diarrhea, encephalomyocarditis virus, parainfluenza, vesicular stomatitis virus., microscope slides, PBS, incubator with humidifying chamber at 36° C., Evan's blue coutner stain, DI Water, fluorescent microscope, trypsin, serum containing media, acetone, T25 Flask.

Procedure

Cells (described in Sections B and C) are trypsinized to detach them from the T25 flask and sufficient media is added to neutralize trypsin activity. A drop of cell suspension is placed on each microscope slide and allowed to air dry. A slide for each fluorescent antibody is prepared. Cells are fixed by immersion in acetone for five minutes. Each fluorescent antibody solution is placed on each slide to cover cells and the slides are incubated in humidifying chamber in incubator at 36° C. for 30 minutes. The slides are then washed in PBS for five minutes. The wash is repeated in fresh PBS for five minutes followed by a rinse with DI water.

The cells are counterstained by placing Evan's blue solution on each slide to cover cells for five minutes at room temperature. The slides are then washed in PBS for five minutes. The wash is repeated in fresh PBS for five minutes followed by a rinse with DI water. The slides are then allowed to air dry. Each slide is inspected under a fluorescent microscope. Any fluorescent inclusion bodies characteristic of infection are considered a positive result for the presence of virus.

F. Procedures for Defining Bacteremic Pigs

Materials

Anaerobic BMB agar (5% sheep blood, vitamin K and hemin [BMB/blood]), chocolate Agar with Iso Vitalex, Sabaroud dextrose agar/Emmons, 70% isopropyl alcohol swabs, betadine solution, 5% $CO_2$ incubator at 35–37° C., anaerobic blood agar plate, gram stain reagents (Columbia Broth Media), aerobic blood culture media (anaerobic brain heart infuision with vitamin K& hemin), septicheck media system, vitek bacterial identification system, laminar flow hood, microscope, and bacteroids and Bacillus stocks Procedure Under a laminar flow hood, disinfect the tops of bottles for aerobic and anaerobic blood cultures of blood obtained from pig with 70% isopropyl alcohol, then with betadine The rubber stopper and cap from the aerobic blood culture bottle are removed and a renal septicheck media system is attached to the bottle. The bottles are incubated in 5% $CO_2$ for 21 days at 35–37° C., and observed daily for any signs of bacterial growth (i.e. gas bubbles, turbidity, discoloration or discrete clumps). Negative controls consisting of 5 cc of sterile saline in each bottle and positive controls consisting of *Bacillus subtilis* in the aerobic bottle and *Bacteriodes Vulgaris* in the anaerobic bottle are used. If signs of bacterial growth are observed, a Gram stain is prepared and viewed microscopically at 100x oil immersion for the presence of any bacteria or fungi. The positive bottles are then subcultured onto both chocolate agar plates with Iso Vitlex and onto BMB plates. The chocolate plate is incubated at 35–37° C. in 5% $CO_2$ for 24 hours and the BMB anaerobically at 35–37° C. for 48 hours. Any yeast or fungi that is in evidence at gram stain is subcultured onto a Sabaroud dextrose/Emmons plate. The Vitek automated system is used to identify bacteria and yeast. Fungi are identified via their macroscopic and microscopic characteristic. If no signs of growth are observed at the end of 21 days, gram stain is prepared and observed microscopically for the presence of bacteria and fungi.

Absence of growth in the negative control bottles and presence of growth in the positive control bottles indicates a valid test. The absence of any signs of growth in both the aerobic and anaerobic blood culture bottles, as well as no organisms seen on gram stain indicates a negative blood culture. The presence and identification of microorganism(s) in either the aerobic or anaerobic blood culture bottle indicates of a positive blood culture; this typicall is due to a bacteremic state.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A method of treating a subject having chronic pain or spasticity, wherein the chronic pain or spasticity results from an elevated level of neuron excitability in the spinal cord of the subject, comprising administering into the spinal cord of the subject a composition comprising a population of isolated, primary, serotonergic or gamma-amino butyric acid (GABA)—producing neurons obtained from a fetus such that chronic pain or spasticity resulting from an elevated level of neuron excitability in the spinal cord of the subject is treated.

2. A method of treating a subject having chronic pain resulting from spinal cord injury comprising administering into the spinal cord of the subject a composition consisting essentially of a population of isolated GABA-producing neurons, such that chronic pain resulting from spinal cord injury is treated.

3. The method of claim 1, wherein the neurons are obtained from the lateral ganglionic eminence of fetal brain.

4. The method of claim 1, wherein the neurons are delivered into the spinal dorsal horn of the subject.

5. The method of claim 1, wherein the neurons are delivered into the subarachnoid space of the spinal cord of the subject.

6. The method of claim 1 wherein the population of neurons produce gamma-aminobutyric acid (GABA).

7. The method of claim 1 wherein the neurons produce 5 hydroxy-tryptamine.

8. The method of claim 1, wherein the neurons are human neurons.

9. The method of claim 1, wherein the neurons are porcine neurons.

10. The method of claim 1 wherein the neurons, in unmodified form, have at least one antigen on the cell surface which is capable of stimulating an immune response against the cells in the subject, wherein the antigen on the surface or the cells is altered such that lysis of the neurons does not occur upon introduction of the neurons into the subject and the stimulation of an immune response is inhibited.

11. The method of claim 10, wherein, prior to administration to the subject, the neurons are contacted with a non-complement fixing antibody or non-complement fixing fragment of an antibody which binds to at least one antigen on the cell surface which is capable of stimulating an immune response against the cells in the subject to alter the antigen on the cell surface that an immune response against the cells is inhibited.

12. The method of claim 11, wherein, prior to administration to the subject, the neurons are contacted with at least one anti-MHC class I antibody or fragment thereof, which binds to the MHC class I antigen on the cell surface.

13. The method of claim 12, wherein the anti-MHC class I antibody is an anti-MHC class I F(ab')$_2$ fragment.

14. The method of claim 12, wherein, prior to administration to the subject, the cells are contacted with a F(ab')$_2$ fragment of a W6/32 monoclonal antibody such that an immune response against the cell is inhibited.

15. The method of claim 1 wherein the composition further comprises at least one of the agents or factors selected from the group consisting of neurotrophic factors and anti-inflammatory agents.

16. The method of claim 15 wherein the neutrophic factor is selected from the group consisting of brain derived neutrotrophic factor, ciliary neutrotrophic factor, neurotrophin-3, neurotrophin 4/5, nerve growth factor, acidic fibroblast growth factor, basic fibroblast growth factor, platelet-derived growth factor, thyrotropin releasing hormone, epidermal growth factor, amphiregulin, transforming growth factor, transforming growth factor β, insulin-like growth factor.

17. The method of claim 15, wherein the agent is an anti-inflammatory agent.

18. The method of claim 17, wherein the anti-inflammatory agent is selected from the group consisting of: methylprednisolone, cyclosporin A, or FK506.

19. The method of claim 9, wherein the porcine neurons are obtained from a pig which predetermined to be free from at least one organism selected from the group consisting of zoonotic, cross-placental and neurotropic organisms.

20. The method of claim 3 wherein the neurons are porcine neurons.

21. The method of claim 20, wherein the neurons are obtained from the lateral ganglionic eminence of an fetal pig between about days 30 and 40 of gestation.

22. The method of claim 1 wherein, prior to delivery to the subject, the cells are contacted with a F(ab')$_2$ fragment of a W6/32 or PT85 monoclonal antibody such that an immune response against the cells is inhibited.

23. The method of claim 1 wherein the subject is a human.

24. A method of treating a subject having spasticity resulting from spinal cord injury comprising administering into the spinal cord of the subject a composition consisting essentially of a population of isolated GABA-producing neurons such that spasticity resulting from spinal cord injury is treated.

25. The method of claim 1, wherein the level of neuron excitability of spinal cord origin is decreased.

* * * * *

UNITED STATES PATENT AND TRADEMARK OFFICE
CERTIFICATE OF CORRECTION

PATENT NO. : 6,444,205 B2
DATED : September 3, 2002
INVENTOR(S) : Jonathan Dinsmore et al.

It is certified that error appears in the above-identified patent and that said Letters Patent is hereby corrected as shown below:

Column 28,
Lines 39 and 40, "...against the cells in the subject, wherein the antigen on the surface or the cells is altered such that lysis of the neurons..." should read -- ... against the cells in the subject, wherein the antigen on the surface of the cells is altered such that lysis of the neurons... --

Column 28, lines 66 and 67 through Column 29, line 1,
"The method of claim 15 wherein the neutrophic factor is selected from the group consisting of brain derived neutrotrophic factor, ciliary neutrotrophic factor,..." should read -- The method of claim 15 wherein the neurotrophic factor is selected from the group consisting of brain derived neurotrophic factor, ciliary neurotrophic factor,... --

Signed and Sealed this

Twenty-fifth Day of March, 2003

JAMES E. ROGAN
*Director of the United States Patent and Trademark Office*